(12) United States Patent
Burnstein

(10) Patent No.: US 10,231,952 B2
(45) Date of Patent: Mar. 19, 2019

(54) USE OF ARGININE VASOPRESSIN RECEPTOR ANTAGONISTS FOR THE TREATMENT OF PROSTATE CANCER

(71) Applicant: UNIVERSITY OF MIAMI, Miami, FL (US)

(72) Inventor: Kerry L. Burnstein, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 11 days.

(21) Appl. No.: 14/811,354

(22) Filed: Jul. 28, 2015

(65) Prior Publication Data

US 2016/0022635 A1 Jan. 28, 2016

Related U.S. Application Data

(60) Provisional application No. 62/029,779, filed on Jul. 28, 2014.

(51) Int. Cl.
| | | |
|---|---|---|
| *A61K 31/404* | (2006.01) | |
| *A61K 31/58* | (2006.01) | |
| *A61K 45/06* | (2006.01) | |
| *A61K 31/00* | (2006.01) | |

(52) U.S. Cl.
CPC ............ *A61K 31/404* (2013.01); *A61K 31/00* (2013.01); *A61K 31/58* (2013.01); *A61K 45/06* (2013.01)

(58) Field of Classification Search
None
See application file for complete search history.

(56) References Cited

U.S. PATENT DOCUMENTS

2012/0207733 A1* 8/2012 Jacky ................. A61K 38/4893
424/94.3

FOREIGN PATENT DOCUMENTS

WO WO 2011047383 A1 * 4/2011 ....... A61K 39/39558

OTHER PUBLICATIONS

Zhong et al. (Molecular Cancer Research, 2010, 8:1164-1172).*
Weber et al. (Hypertension, 1997, 30:1121-1127).*
Fizazi et al. (Lancet Oncology, 2012, 13:983-992).*
Kirby et al. (BJU International, 2009, 104:1580-1584).*
Peacock (Open Access Dissertations, 2013, 1091).*
Uemura et al. (International Journal of Clinical Oncology, 2005, 10:405-410).*
Holt et al. (Journal of Cardiothoracic and Vascular Anesthesia, 2010, 24:330-347).*
Zhu et al. (Neuromodulation: Technolcoy at the Neural Interface, 2016, 19:598-506).*
Feldman et al. (New England of Journal of Medicine, 2005, 352:1884-1890).*
Bockaert, J. et al., GPCR interacting proteins (GIP), *Pharmacol. Ther.*, 103(3):203-221 (2004).
Bockaert, J. et al., GPCR interacting proteins (GIPs) in the nervous system: Roles in physiology and pathologies, *Annu. Rev. Pharmacol. Toxicol.*, 50:89-109 2010).
Brouard, R. et al., Safety, tolerability, and pharmacokinetics of SR 49059, a V1a vasopressin receptor antagonist, after repeated oral administration in healthy volunteers, *Adv. Exp. Med. Biol.*, 449:455-465 (1998).
Cai, C. et al., Androgen receptor gene expression in prostate cancer is directly suppressed by the androgen receptor through recruitment of lysine-specific demethylase 1, *Cancer Cell*, 20(4):457-71 (2011).
Chandran, U.R. et al., Gene expression profiles of prostate cancer reveal involvement of multiple molecular pathways in the metastatic process, *BMC Cancer*, 7:64 (2007).
Decaux, G. et al., Non-peptide arginine-vasopressin antagonists: the vaptans, *Lancet*, 371:1624-1632 (2008).
Dehm, S.M. et al., Splicing of a novel androgen receptor exon generates a constitutively active androgen receptor that mediates prostate cancer therapy resistance, *Cancer Res.*, 68(13):5469-5477 (2008).
Deocampo, N.D. et al., The role of PTEN in the progression and survival of prostate cancer, *Minerva Endocrinol.*, 28(2):145-53 (2003).
Fahrenholtz, C.D. et al., Preclinical efficacy of growth hormone-releasing hormone antagonists for androgen-dependent and castration-resistant human prostate cancer, *Proc. Natl. Acad. Sci. USA*, 111(3):1084-9 (2014).
Fahrenholtz, C.D. et al., Targeting IGF-1R with ganitumab inhibits tumorigenesis and increases durability of response to androgen-deprivation therapy in VCaP prostate cancer xenografts, *Mol Cancer Ther*, 12(4):394-404 (2013).
Gaj, T. et al., ZFN, TALEN, and CRISPR/Cas-based methods for genome engineering, *Trends Biotechnol.*, 31(7):397-405 (2013).
Guo, Z. et al., A novel androgen receptor splice variant is up-regulated during prostate cancer progression and promotes androgen depletion-resistant growth, *Cancer Res*, 69(6):2305-2313 (2009).
Havens, A.M. et al., An in vivo mouse model for human prostate cancer metastasis, *Neoplasia.* 10(4):371-80 (2008).
Iannucci, N.B. et al, Antiproliferative effect of 1-deamino-8-D-arginine vasopressin analogs on human breast cancer cells, *Future Med. Chem.*, 3(16):1987-93 (2011).
Ishteiwy, R.A. et al., The microRNA—23b/-27b cluster suppresses the metastatic phenotype of castration-resistant prostate cancer cells, *PLoS One*, 7(12):e52106 (2012).

(Continued)

*Primary Examiner* — Julie Wu
(74) *Attorney, Agent, or Firm* — Marshall, Gerstein & Borun LLP

(57) ABSTRACT

Described herein are methods of decreasing the proliferation of prostate cancer cells in a mammalian subject by administering to a subject in need thereof a composition comprising an AVPR antagonist in amount effective to decrease proliferation of the cancer cells. Also provided are methods of inducing prostate cancer cell death (or decreasing invasion migration of the prostate cancer cells) in a mammalian subject by administering to a subject in need thereof a composition comprising an AVPR antagonist.

13 Claims, 14 Drawing Sheets

Specification includes a Sequence Listing.

(56) References Cited

OTHER PUBLICATIONS

Jenkins, D.E. et al., In vivo monitoring of tumor relapse and metastasis using bioluminescent PC-3M-luc-C6 cells in murine models of human prostate cancer, *Clin. Exp. Metastasis*, 20(8):745-756 (2003).

Kim, J.I. et al., G-protein coupled receptor kinase 5 regulates prostate tumor growth, *J. Urol.*, 187(1):322-9 (2012).

Korenchuk S. et al., VCaP, a cell-based model system of human prostate cancer, *In Vivo*, 15(2):163-8 (2001).

Koshimizu, T.A. et al., Vasopressin V1a and V1b receptors: from molecules to physiological systems, *Physiol. Rev.*, 92(4):1813-1864 (2012).

Kostrzewska, A. et al., Effects of the vasopressin V1a receptor antagonist, SR 49059, on the response of human uterine arteries to vasopressin and other vasoactive substances, *Acta. Obstet. Gynecol. Scand.*, 77(1):3-7 (1998).

Lappano, R. et al., G protein-coupled receptors: novel targets for drug discovery in cancer, *Nat. Rev. Drug. Discov.*, 10(1):47-60 (2011).

Lefkowitz, R.J. et al., Transduction of receptor signals by beta-arrestins, *Science*, 308(5721): 512-517 (2005).

Lefkowitz, R.J., Seven transmembrane receptors: something old, something new, *Acta Physiol.* (Oxf), 190(1): 9-19 (2007).

Lemmens-Gruber, R. et al., Vasopressin antagonists, *Cell Mol. Life Sci.*, 63(15):1766-1779 (2006).

Li, Y. et al., Androgen Receptor Splice Variants Mediate Enzalutamide Resistance in Castration-Resistant Prostate Cancer Cell Lines, *Cancer Res*, 73(2):483-9 (2013).

Lyons, L.S. et al., Ligand-independent activation of androgen receptors by Rho GTPase signaling in prostate cancer, *Mol. Endocrinol*, 22(3):597-608 (2008).

Magnon, C. et al., Autonomic nerve development contributes to prostate cancer progression, *Science*, 341(6142):1236361 (2013).

Manaenko, A. et al., Post-treatment with SR49059 improves outcomes following an intracerebral hemorrhagic stroke in mice, *Acta Neurochir. Suppl.*, 111:191-196 (2011).

Manning, M. et al., Oxytocin and vasopressin agonists and antagonists as research tools and potential therapeutics, *J. Neuroendocrinol*, 24(4):609-28 (2012).

Mostaghel, E.A. et al., Resistance to CYP17A1 inhibition with abiraterone in castration-resistant prostate cancer: induction of steroidogenesis and androgen receptor splice variants, *Clin. Cancer Res*, 17(18):5913-5925 (2011).

Nishimura, A. et al., Structural basis for the specific inhibition of heterotrimeric Gq protein by a small molecule, *Proc. Natl. Acad. Sci. USA*, 107(31):13666-71 (2010).

North, W.G. et al., MCF-7 breast cancer cells express normal forms of all vasopressin receptors plus an abnormal V2R, *Peptides*, 20(7):837-42 (1999).

North, W.G. et al., Expression of all known vasopressin receptor subtypes by small cell tumors implies a multifaceted role for this neuropeptide, *Cancer Res*, 58(9):1866-71 (1998).

Park, S.I. et al., Pre-clinical mouse models of human prostate cancer and their utility in drug discovery, *Curr. Protoc. Pharmacol.*, Chapter 14:Unit 14.15 (2010).

Peacock, S.O. et al., Vav3 enhances androgen receptor splice variant activity and is critical for castration-resistant prostate cancer growth and survival, *Mol. Endocrinol.*, 26(12):1967-1979 (2012).

Perkins, L.M. et al., Quantification of P450scc, P450(17) alpha, and iron sulfur protein reductase in Leydig cells and adrenals of inbred strains of mice, *Endocrinology*, 123(6):2675-82 (1988).

Rao, S. et al., A novel nuclear role for the Vav3 nucleotide exchange factor in androgen receptor coactivation in prostate cancer, *Oncogene*, 31(6):716-727 (2012).

Rhodes, D.R. et al., ONCOMINE: a cancer microarray database and integrated data-mining platform, *Neoplasia*, 6(1):1-6 (2004).

Rubin, M.A. et al., Common gene rearrangements in prostate cancer, *J. Clin. Oncol.*, 29(27):3659-68 (2011).

Scatena, C.D. et al., Imaging of bioluminescent LNCaP-luc-M6 tumors: a new animal model for the study of metastatic human prostate cancer, *Prostate*, 59(3):292-303 (2004).

Serradeil-Le Gal, C. et al., Biochemical and pharmacological properties of SR 49059, a new, potent, nonpeptide antagonist of rat and human vasopressin V1a receptors. *J Clin Invest*, 92(1):224-231 (1993).

Sobel, R.E. et al., Cell lines used in prostate cancer research: a compendium of old and new lines—part 1, *J. Urol*, 173(2):342-359 (2005).

Sobel, R.E. et al., Cell lines used in prostate cancer research: a compendium of old and new lines—part 2. *J. Urol*, 173(2):360-372 (2005).

Steinwall, M. et al., The effect of relcovaptan (SR 49059), an orally active vasopressin V1a receptor antagonist, on uterine contractions in preterm labor, *Gynecol Endocrinol*, 20(2):104-9 (2005).

Tamura, K. et al., Molecular features of hormone-refractory prostate cancer cells by genome-wide gene expression profiles, *Cancer Res*, 67(11):5117-5125 (2007).

Thibonnier, M. et al., Effects of the nonpeptide V(1) vasopressin receptor antagonist SR49059 in hypertensive patients, *Hypertension*, 34(6):1293-300 (1999).

Tribollet, E. et al., Binding of the non-peptide vasopressin V1a receptor antagonist SR-49059 in the rat brain: an in vitro and in vivo autoradiographic study, *Neuroendocrinology*, 69(2):113-20 (1999).

Wang, M., Isolation and characterization of PC-3 human prostatic tumor sublines which preferentially metastasize to select organs in S.C.I.D. mice, *Differentiation*, 48(2):115-125 (1991).

Watson, P.A. et al., Constitutively active androgen receptor splice variants expressed in castration-resistant prostate cancer require full-length androgen receptor, *Proc. Natl. Acad. Sci. USA*, 107(39):16759-16765 (2010).

Yap, T.A. et al., The changing therapeutic landscape of castration-resistant prostate cancer. Nature reviews, *Clinical oncology*, 8(10):597-610 (2011).

Zhu, W. et al., Arginine vasopressin enhances cell survival via a G protein-coupled receptor kinase 2/β-arrestin1/extracellular-regulated kinase 1/2-dependent pathway in H9c2 cells, *Mol Pharmacol.*, 84(2):227-35 (2013).

\* cited by examiner

USE OF ARGININE VASOPRESSIN RECEPTOR ANTAGONISTS FOR THE TREATMENT OF PROSTATE CANCER

CROSS-REFERENCE TO RELATED APPLICATION

The present application claims the benefit of priority of U.S. Provisional Application No. 62/029,779, filed Jul. 28, 2014, the disclosure of which is incorporated herein by reference in its entirety.

STATEMENT AS TO FEDERALLY SPONSORED RESEARCH

This invention was made with government support under Grant Number RO1 CA132200 awarded by the National Cancer Institute and Grant Number F30AG038275 awarded by the National Institute on Aging. The government has certain rights in the invention.

FIELD OF THE INVENTION

The present disclosure is directed to materials and methods for the treatment of prostate cancer.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII text file named "48815A_SeqListing.txt"; 5,276 bytes, created Jul. 28, 2015.

BACKGROUND

For more than half a century, the standard of care for this advanced stage prostate cancer (PC) is androgen deprivation therapy. Androgen deprivation generally leads to disease remission. Unfortunately, the effectiveness of this regimen is temporary (1-3 years). The recurrent disease is termed "castration resistant." Castration resistant PC (CPRC) is treated using chemotherapeutic drugs such as docetaxel, which provide a modest but significant survival benefit (3). While new agents including the steroid biosynthetic enzyme Cyp17 inhibitor, abiraterone acetate, and the androgen receptor (AR) antagonist, MDV3100 (enzalutamide), significantly extend the survival of men whose PC progresses following chemotherapy, metastatic CRPC remains incurable (3). There is a critical need for new therapies for CRPC. Moreover, since virtually all men progress to CRPC following androgen deprivation therapy, increasing the durability of this treatment is also an important and essential goal.

SUMMARY

The present application is based, at least in part, on the discovery that inhibition or down-regulation of an arginine vasopressin receptor (AVPR) results in decreased proliferation of prostate cancer cells.

In one aspect, the disclosure provides a method of treating prostate cancer in a mammalian subject comprising administering a composition comprising an arginine vasopressin receptor (AVPR) antagonist in an amount effective to treat the prostate cancer in the subject. In another aspect, the disclosure provides a method of decreasing the proliferation of prostate cancer cells in a mammalian subject, comprising contacting the cells with a composition comprising an arginine vasopressin receptor (AVPR) antagonist in an amount effective to decrease proliferation of the cancer cells in the subject. In another aspect, the disclosure provides a method of inducing prostate cancer cell death in a mammalian subject, comprising contacting the cells with a composition comprising an arginine vasopressin receptor (AVPR) antagonist in an amount effective to induce prostate cancer cell death in the subject. In some embodiments, the AVPR is selected from the group consisting of AVPR1a, AVPR1b and AVPR2.

Exemplary AVPR antagonists for use in the methods described herein include, but are not limited to, a small molecule antagonist, an antibody antagonist, a peptide antagonist and an oligonucleotide antagonist. In some embodiments, the AVPR antagonist is selected from the group consisting of Relcovaptan, OPC-21268, PF-00738245, SRX-251, SRX-246, Conivaptan, Nelivaptan, Lixivaptan, Mozavaptan, Satavaptan, Tolvaptan and demeclocycline. In some embodiments, the AVPR antagonist is Relcovaptan (SR49059).

The mammalian subject that is administered a composition comprising the AVPR antagonist is preferably human.

The methods described herein optionally comprise administering an additional therapeutic to the subject in combination with the AVPR antagonist. In some embodiments, the methods described herein further comprise administering an androgen receptor antagonist to the subject. Exemplary androgen receptor antagonists include, but are not limited to, Enzalutamide, Bicalutamide, Ostarine, Flutamide, Cyproterone acetate, Gugguisterone, Nilutamide, PF998245, (R)-Bicalutamide, 1,1-Dichloro-2,2-bis(4-chlorophenyl)ethene, ARN-509 and MDV-3100.

In some embodiments, the methods described herein further comprise administering an inhibitor of androgen synthesis to the subject. An exemplary inhibitor of androgen synthesis is Abiraterone acetate.

With respect to any combination treatment or therapy regimens described herein, the AVPR antagonist composition can be administered simultaneously with the other active agents, which may be in admixture with the AVPR antagonist, or may be in a separate composition. Each composition preferably includes a pharmaceutically acceptable diluent, adjuvant, or carrier. When the agents are separately administered, they may be administered in any order.

Also described herein is an arginine vasopressin receptor (AVPR) antagonist for use in decreasing the proliferation of prostate cancer cells (or for inducing prostate cancer cell death) in a mammalian subject.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicant(s) by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION

The present application is based, at least in part, on the discovery that arginine vasopressin receptor type 1a (AVPR1a) in prostate cancer (PC) cells is a driver of aggressive growth of castration resistant prostate cancer (CRPC). Successful AVPR1a antagonism in any of the clinical settings (e.g., CRPC, progression to CRPC, metastasis) described herein will be a major advance for PC therapy.

Androgen receptor (AR) signaling is maintained in CRPC, which provides an explanation for the efficacy of drugs such as abiraterone and enzalutamide that inhibit androgen production or target AR directly (3). Unfortunately, up-regulation of constitutively active AR splice variants often occurs in CRPC and is linked to poor prognosis (4,5). These receptor variants typically lack ligand binding domains and are therefore resistant to treatment paradigms that derive therapeutic efficacy by inhibiting this AR domain (e.g., abiraterone and enzalutamide). Further, AR splice variants appear to be upregulated in PC tumors in response to abiraterone and enzalutamide, which may lead to drug resistance (6,7). The arginine vasopressin receptor type 1a gene (AVPR1a) is identified herein as an AR splice variant-regulated gene and a novel therapeutic target for PC. Interestingly, AVPR1a expression is not restricted to AR splice variant-expressing PC cells suggesting that, while AVPR1a is a transcriptional target of AR splice variants, expression of this gene can be maintained by additional mechanisms. Depletion of AVPR1a with subtype-specific shRNAs or targeting AVPR1a using a selective antagonist caused prostate cancer cell death (regardless of AR or AR splice variant status) but did not affect normal prostate epithelial cell proliferation or survival.

Figure 1A:
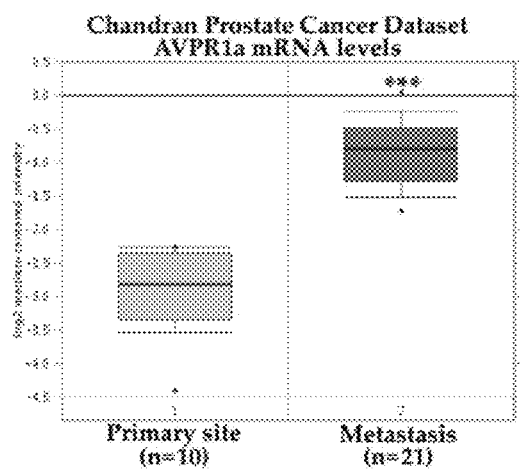
FIGS. 1A-1C. AVPR1a is expressed at highest levels in metastasis versus primary prostate cancer sites. (A) The Chandran Prostate Cancer Dataset show a greater than fourfold increase in AVPR1a mRNA levels in metastatic samples (n=21) versus primary site samples (n=10). (B) The Tamura Prostate Cancer Dataset show a greater than 1.7 fold increase in AVPR1a mRNA levels in metastatic samples (n=12) versus primary site samples (n=23). (*, $p<0.01$; ***, $p<0.001$). (C) The Tamura Prostate Cancer Dataset primary site samples can be further subdivided into hormone naïve and hormone refractory samples, which indicate that AVPR1a is highest in metastatic and CRPC compared to primary site disease.

Analysis of the Oncomine database (8), revealed that the two distinct datasets with metastatic castration resistant prostate cancer (CRPC) human specimens showed elevations of AVPR1a mRNA in metastatic vs. primary site (prostate) human cancer (4.3-fold increase in Chandran and 1.7 fold in Tamura datasets) (9,10) (FIG. 1A, B). The metastatic samples from both datasets were castration resistant (obtained from patients whose disease progressed despite androgen deprivation therapy). However, in the Tamura dataset, the primary site cancer specimens were a mix of 13 CRPC and 10 hormone naïve samples (from patients who did not undergo androgen deprivation). Further stratification of the primary site (localized) samples shows that AVPR1a is higher in CRPC localized in the prostate compared to hormone naïve primary site tumors (FIG. 1C). The Chandran and Tamura datasets do not contain information from normal/benign prostate tissues. Analyses of additional datasets in Oncomine with PC and benign specimens indicate that AVPR1a is somewhat elevated in PC compared to normal/benign prostate tissues. Notably, the AVPR1a gene exhibits a significant increase in copy number in human PC specimens (Oncomine/The Cancer Genome Atlas TCGA). These results indicate that AVPR1a is upregulated particularly in advanced human PC compared to primary site cancer and benign prostate tissues.

Methods of Treatment

In one aspect, the disclosure provides a method of treating prostate cancer in a mammalian subject comprising administering a composition comprising an arginine vasopressin receptor (AVPR) antagonist to the subject in an amount effective to treat the prostate cancer in the subject. Also provided is a method of decreasing the proliferation of prostate cancer cells in a mammalian subject, comprising contact the cells with a composition comprising an arginine vasopressin receptor (AVPR) antagonist in an amount effective to decrease proliferation of the cancer cells in the subject. In some embodiments, the prostate cancer is metastatic prostate cancer.

There are three arginine vasopressin receptor subtypes (V1a, V1b and V2) that mediate the physiologic effects of the posterior pituitary gland hormone, arginine vasopressin (AVP, also known as antidiuretic hormone). These receptors belong to the large class of G protein coupled receptors (GPCRs). In some embodiments, the AVPR is AVPR1a. The amino acid sequence of human AVPR1a is set forth in Genbank Accession No. NP_000697 and SEQ ID NO: 1 AVPR1a are found in vascular smooth muscle cells, cardiomyocytes, kidney, liver, brain and certain other tissues (12,13).

In other embodiments, the AVPR is AVPR1b. The amino acid sequence of AVPR1b is set forth in Genbank Accession No. NP_000698.1. AVPR1b belongs to the subfamily of G-protein coupled receptors. Its activity is mediated by G proteins which stimulate a phosphatidylinositol-calcium second messenger system.

In other embodiments, the AVPR is AVPR2. The amino acid sequence of AVPR2 is set forth in Genbank Accession No. NP_000045.1. AVPR2 belongs to the subfamily of G-protein-coupled receptors. Its activity is mediated by the Gs type of G proteins, which stimulate adenylate cyclase. AVPR2 is expressed in the kidney tubule, predominantly in the membrane of cells of the distal convoluted tubule and collecting ducts, in fetal lung tissue and lung cancer, the last two being associated with alternative splicing. AVPR2 is also expressed outside the kidney, and, when stimulated, a variety of clotting factors are released into the bloodstream. In the kidney, AVPR2's primary property is to respond to arginine vasopressin by stimulating mechanisms that concentrate the urine and maintain water homeostasis in the organism. When the function of AVPR2 is lost, the disease Nephrogenic Diabetes Insipidus (NDI) results.

The methods described herein comprising administering to the subject in need thereof (or contacting prostate cells with) a composition comprising an AVPR antagonist. In some embodiments, the AVPR antagonist is selected from the group consisting of a small molecule, an antibody, a peptide antagonist and an oligonucleotide antagonist molecule.

Small Molecule Antagonists

In some embodiments, the AVPR antagonist is a small molecule that selectively inhibits AVPR1a. A molecule that "selectively" inhibits AVPR1a refers to a molecule that inhibits AVPR1a and not AVPR1b or AVPR2. Exemplary small molecules that selectively inhibit AVPR1a include, but are not limited to, Relcovaptan, SRX-251, SRX-246 and PF-184563. Relcovaptan (SR049059), is highly selective for AVPR1a in human tissues with high affinity for a single population of binding sites (Kd 15 pM) (17). The structure of Relcovaptan is provided below:

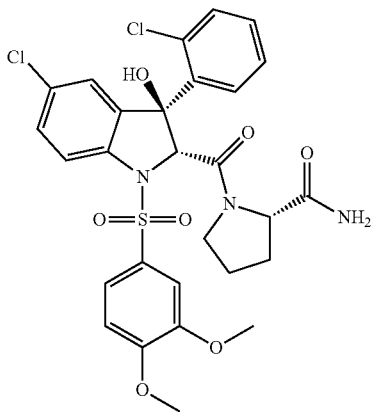 [SMILES: COc1ccc(S(=O)(=O)N2c3ccc(Cl)cc3[C@](O)(c3ccccc3Cl)[C@@H]2C(=O)N2CCC[C@H]2C(N)=O)cc1OC]

Relcovaptan, developed by Sanofi, also is a selective antagonist for AVPR1a in rodents (17). Relcovaptan is orally active, lacks partial agonist activity, does not cross the blood brain barrier and has been used in several clinical trials for indications including: preterm labor, dysmenorrhea, primary aldosteronism, Raynaud's disease and hypertension (2,12, 18-20). Relcovaptan is an orally active, small molecule inhibitor that does not cross the blood brain barrier (1). Conivaptan is the only FDA-approved AVP receptor antagonist and non-selectively blocks both AVP type V1a and V2 receptors (16). This drug is approved for hospitalized patients with euvolemic hyponatremia (low plasma sodium with normal water volume) (16).

In some embodiments, the AVPR antagonist is a small molecule that selectively inhibits AVPR1b. An exemplary small molecule that selectively inhibits AVPR1b is Nelivaptan.

In some embodiments, the AVPR antagonist is a small molecule that selectively inhibits AVPR2. Exemplary small molecules that selectively inhibit AVPR2 include, but are not limited to Tolvaptan, Lixivaptan, Mozavaptan and Satavaptan.

Antibody Antagonists

In some embodiments, the AVPR antagonist is an antibody (e.g., monoclonal and polyclonal antibodies, single chain antibodies, chimeric antibodies, bifunctional/bispecific antibodies, humanized antibodies, human antibodies, and complementarity determining region (CDR)-grafted antibodies, including compounds that include CDR sequences specifically recognizing AVPR1a, AVPR1b or AVPR2). In various aspects, the antibody is an IgG antibody having full length heavy and light chains. Antibodies can be human antibodies which are produced and identified according to methods described in WO 93/11236, which is incorporated herein by reference in its entirety. The term "specific for," when used to describe antibodies of the invention, indicates that the variable regions of the antibodies of the invention recognize and bind the polypeptide of interest (AVPR) with a detectable preference (i.e., able to distinguish the polypeptide of interest from other known polypeptides of the same family (e.g., other GPCRs), by virtue of measurable differences in binding affinity, despite the possible existence of localized sequence identity, homology, or similarity between family members). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies of the invention can be produced using any method well known in the art.

Various procedures known in the art may be used for the production of polyclonal antibodies to AVPR polypeptides. For the production of antibodies, various host animals (including but not limited to rabbits, mice, rats, hamsters, and the like) are immunized by injection with an AVPR peptide. Various adjuvants may be used to increase the immunological response, depending on the host species, including but not limited to Freund's (complete and incomplete) adjuvant, mineral gels such as aluminium hydroxide, surface active substances such as lysolecithin, pluronic polyols, polyanions, oil emulsions, keyhole limpet hemocyanins, dinitrophenol, and potentially useful human adjuvants such as BCG (Bacillus Calmette-Guerin) and *Corynebacterium parvum*.

A monoclonal antibody to an AVPR peptide may be prepared by using any technique which provides for the production of antibody molecules by continuous cell lines in culture. These include but are not limited to the hybridoma technique originally described by Köhler et al., Nature, 256: 495-497 (1975), and the more recent human B-cell hybridoma technique [Kosbor et al., Immunology Today, 4: 72 (1983)] and the EBV-hybridoma technique [Cole et al., Monoclonal Antibodies and Cancer Therapy, Alan R Liss, Inc., pp. 77-96 (1985), all specifically incorporated herein by reference]. Antibodies against an AVPR peptide also may be produced in bacteria from cloned immunoglobulin cDNAs. With the use of the recombinant phage antibody system it may be possible to quickly produce and select antibodies in bacterial cultures and to genetically manipulate their structure. The term "monoclonal antibody" as used herein refers to a homogenous population of antibodies. Hybridoma technology is one method of generating monoclonal antibodies. Other methods are known in the art and are discussed herein.

In addition to the production of monoclonal antibodies, techniques developed for the production of "chimeric antibodies," the splicing of mouse antibody genes to human antibody genes to obtain a molecule with appropriate antigen specificity and biological activity can be used [Morrison et al., Proc. Natl. Acad. Sci. 81:6851-6855 (1984); Neuberger et al., Nature 312:604-608 (1984); Takeda et al., Nature 314:452-454 (1985)]. Alternatively, techniques described for the production of single-chain antibodies (U.S. Pat. No. 4,946,778) can be adapted to produce AVPR peptide-specific single chain antibodies.

Rapid, large scale recombinant methods for generating antibodies may be employed, such as phage display [Hoogenboom et al., J. Mol. Biol. 227: 381, (1991); Marks et al., J. Mol. Biol. 222: 581, (1991)] or ribosome display methods, optionally followed by affinity maturation [see, e.g., Ouwehand et al., Vox Sang 74(Suppl 2):223 232 (1998); Rader et al., Proc. Natl. Acad. Sci. USA 95:8910 8915 (1998); Dall'Acqua et al., Curr. Opin. Struct. Biol. 8:443 450, (1998)]. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach.

Antibody fragments are also provided by the invention. "Antibody fragments" comprise a portion of an intact immunoglobulin that binds an antigen, e.g., an antigen binding or variable region of the intact antibody, and include multispecific (bispecific, trispecific, etc.) antibodies formed from antibody fragments. Fragments of immunoglobulins may be produced by recombinant DNA techniques or by enzymatic or chemical cleavage of intact antibodies.

Nonlimiting examples of antibody fragments include Fab, Fab', F(ab')$_2$, Fv (variable region), domain antibodies (dAb, containing a $V_H$ domain) (Ward et al., Nature 341:544-546, 1989), complementarity determining region (CDR) fragments, single-chain antibodies (scFv, containing $V_H$ and $V_L$ domains on a single polypeptide chain) (Bird et al., Science 242:423-426, 1988, and Huston et al., Proc. Natl. Acad. Sci. USA 85:5879-5883, 1988), optionally including a polypeptide linker; and optionally multispecific (Gruber et al., J. Immunol. 152: 5368 (1994)), single chain antibody fragments, diabodies ($V_H$ and $V_L$ domains on a single polypeptide chain that pair with complementary $V_L$ and $V_H$ domains of another chain) ((EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge) (Olafsen, et al., Protein Eng Des Sel. 2004 April; 17(4):315-23), maxibodies (bivalent scFvs covalently attached to the Fc region of an immunoglobulin; Fredericks et al, Protein Engineering, Design & Selection, 17:95-106 (2004) and Powers et al., Journal of Immunological Methods, 251:123-135 (2001)); linear antibodies (tandem Fd segments ($V_H$-$C_{H1}$-$V_H$-$C_{H1}$) (Zapata et al., Protein Eng., 8(10):1057-1062 (1995)); chelating recombinant antibodies (crAb, which can bind to two adjacent epitopes on the sane antigen) (Neri et al., J Mol Biol. 246:367-73, 1995), bibodies (bispecific Fab-scFv) or tribodies (trispecific Fab-(scFv)($_2$)) (Schoonjans et al., J Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain or direct the antibody intracellularly (Mhashilkar et al, EMBO J 14:1542-51, 1995; Wheeler et al., FASEB J. 17:1733-5, 2003), transbodies (cell-permeable antibodies containing a protein transduction domain (PTD) fused to scFv (Heng et al., Med Hypotheses. 64:1105-8, 2005), nanobodies (approximately 15 kDa variable domain of the heavy chain) (Cortez-Retamozo et al., Cancer Research 64:2853-57, 2004), small modular immunopharmaceuticals (SMIPs) (WO03/041600, U.S. Patent publication 20030133939 and US Patent Publication 20030118592), an antigen-binding-domain immunoglobulin fusion protein, a camelized antibody (in which VH recombines with a constant region that contains hinge, $C_{H1}$, $C_{H2}$ and $C_{H3}$ domains) (Desmyter et al., J. Biol. Chem. 276: 26285-90, 2001; Ewert et al., Biochemistry 41:3628-36, 2002; U.S. Patent Publication Nos. 20050136049 and 20050037421), a $V_{HH}$ containing antibody, heavy chain antibodies (HCAbs, homodimers of two heavy chains having the structure $H_2L_2$), or variants or derivatives thereof, and polypeptides that contain at least a portion of an immunoglobulin that is sufficient to confer specific antigen binding to the polypeptide, such as a CDR sequence, as long as the antibody retains the desired biological activity. Such antigen fragments may be produced by the modification of whole antibodies or synthesized de novo using recombinant DNA technologies or peptide synthesis.

Peptide Antagonists

In some embodiments, the AVPR antagonist is a peptide antagonist. Exemplary peptide antagonists include, but are not limited to, neuropeptide antagonists such as SP-G (Arg$^6$, D-Trp$^{7,9}$, N$^{me}$Phe$^8$]-substance P (6-11)) and its analogs ([D-Arg$^1$, D-Phe$^5$, DTrp$^{7,9}$, Leu11-]-substance P (SP-D) and [D-Arg$^1$, DTrp$^{5,7,9}$, Leu$^{11}$-]-substance P (SP-A)) ((MacKinnon et al., Brit. J. Pharmacol., 156:36-47, 2009, the disclosure of which is incorporated herein by reference in its entirety).

Oligonucleotide Antagonists

Oligonucleotide antagonists that may be used according to the methods described herein include oligonucleotides, including pharmaceutically acceptable salts thereof, e.g., sodium salts. Nonlimiting examples include: shRNA, antisense oligonucleotides [Eckstein, Antisense Nucleic Acid Drug Dev., 10: 117-121 (2000); Crooke, Methods Enzymol., 313: 3-45 (2000); Guvakova et al., J. Biol. Chem., 270: 2620-2627 (1995); Manoharan, Biochim. Biophys. Acta, 1489: 117-130 (1999); Baker et al., J. Biol. Chem., 272: 11994-12000 (1997); Kurreck, Eur. J. Biochem., 270: 1628-1644 (2003); Sierakowska et al., Proc. Natl. Acad. Sci. USA, 93: 12840-12844 (1996); Marwick, J. Am. Med. Assoc. 280: 871 (1998); Tomita and Morishita, Curr. Pharm. Des., 10: 797-803 (2004); Gleave and Monia, Nat. Rev. Cancer, 5: 468-479 (2005) and Patil, AAPS J. 7: E61-E77 (2005], triplex oligonucleotides [Francois et al., Nucleic Acids Res., 16: 11431-11440 (1988) and Moser and Dervan, Science, 238: 645-650 (1987)], ribozymes/deoxyribozymes (DNAzymes) [Kruger et al., Tetrahymena. Cell, 31: 147-157 (1982); Uhlenbeck, Nature, 328: 596-600 (1987); Sigurdsson and Eckstein, Trends Biotechnol., 13 286-289 (1995); Kumar et al., Gene Ther., 12: 1486-1493 (2005); Breaker and Joyce, Chem. Biol., 1: 223-229 (1994); Khachigian, Curr. Pharm. Biotechnol., 5: 337-339 (2004); Khachigian, Biochem. Pharmacol., 68: 1023-1025 (2004) and Trulzsch and Wood, J. Neurochem., 88: 257-265 (2004)], small-interfering RNAs/RNAi [Fire et al., Nature, 391: 806-811 (1998); Montgomery et al., Proc. Natl. Acad. Sci. U.S.A., 95: 15502-15507 (1998); Cullen, Nat. Immunol., 3: 597-599 (2002); Hannon, Nature, 418: 244-251 (2002); Bernstein et al., Nature, 409: 363-366 (2001); Nykanen et al., Cell, 107: 309-321 (2001); Gilmore et al., J. Drug Target., 12: 315-340 (2004); Reynolds et al., Nat. Biotechnol., 22: 326-330 (2004); Soutschek et al., Nature, 432173-178 (2004); Ralph et al., Nat. Med., 11: 429-433 (2005); Xia et al., Nat. Med., 10816-820 (2004) and Miller et al., Nucleic Acids Res., 32: 661-668 (2004)], aptamers [Ellington and Szostak, Nature, 346: 818-822 (1990); Doudna et al., Proc. Natl. Acad. Sci. U.S.A., 92: 2355-2359 (1995); Tuerk and Gold, Science, 249: 505-510 (1990); White et al., Mol. Ther., 4: 567-573 (2001); Rusconi et al., Nature, 419: 90-94 (2002); Nimjee et al., Mol. Ther., 14: 408-415 (2006); Gragoudas et al., N. Engl. J. Med., 351: 3805-2816 (2004); Vinores, Curr. Opin. Mol. Ther., 5673-679 (2003) and Kourlas and Schiller et al., Clin. Ther., 28 36-44 (2006)] or decoy oligonucleotides [Morishita et al., Proc. Natl. Acad. Sci. U.S.A., 92: 5855-5859 (1995); Alexander et al., J. Am. Med. Assoc., 294: 2446-2454 (2005); Mann and Dzau, J. Clin. Invest., 106: 1071-1075 (2000) and Nimjee et al., Annu Rev. Med., 56: 555-583 (2005). The foregoing documents are hereby incorporated by reference in their entirety herein, with particular emphasis on those sections of the documents relating to methods of designing, making and using inhibitory oligonucleotides. Commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.).

Oligonucleotide antagonists can be administered directly or delivered to cells by transformation or transfection via a vector, including viral vectors or plasmids, into which has been placed DNA encoding the inhibitory oligonucleotide with the appropriate regulatory sequences, including a promoter, to result in expression of the inhibitory oligonucleotide in the desired cell. Known methods include standard transient transfection, stable transfection and delivery using viruses ranging from retroviruses to adenoviruses. Delivery of nucleic acid inhibitors by replicating or replication-deficient vectors is contemplated. Expression can also be driven by either constitutive or inducible promoter systems (Paddison et al., Methods Mol. Biol. 265:85-100, 2004). In other embodiments, expression may be under the control of tissue or development-specific promoters.

For example, vectors may be introduced by transfection using carrier compositions such as Lipofectamine 2000 (Life Technologies) or Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141:863-74).

Delivery of oligonucleotides may also be achieved via (a) liposomes and liposome-protein conjugates and mixtures; (b) non-liposomal lipid and cationic lipid formulations; (c) activated dendrimer formulations; (d) a polymer formulation such as polyethylenimine (PEI) or pluronic gels or ethylene vinyl acetate copolymer (EVAc), (e) a viral-liposome complex, such as Sendai virus; (f) as a peptide-DNA conjugate; (g) catheters to deliver intra-luminal formulations of the oligonucleotide as a solution or in a complex with a liposome; (h) catheters to deliver to adventitial tissue as a solution or in a complex with a liposome; or (i) bound to a delivery agent such as a targeting moiety, or any suitable carrier such as a peptide or fatty acid molecule. The delivery route will be the one that provides the best inhibitory effect as measured according to the criteria described herein.

Combination Therapy

Combination therapy (or "co-therapy") includes the AVPR antagonist and another agent as part of a specific treatment regimen intended to provide the beneficial effect from the combined action of these therapeutic agents. Additional therapeutic agents or therapies contemplated for use with the AVPR antagonist described herein include, but are not limited to, androgen deprivation therapy, a chemotherapeutic agent, a radiotherapeutic agent, an immunotherapeutic agent, an inhibitor of cellular proliferation, a regulator of programmed cell death, surgery and other agents.

A. Androgen Deprivation Therapy

In some embodiments, androgen deprivation therapy is administered to the subject in combination with the AVPR antagonist. Androgen deprivation therapy comprises the administration of an inhibitor of androgen synthesis to the subject, administration of an androgen receptor antagonist to the subject, administration of a gonadotropin-releasing hormone (GnRH) agonist, administration of a GnRH antagonist or a combination thereof.

In some embodiments, the methods described herein further comprise administering an androgen receptor antagonist to the subject. Exemplary androgen receptor antagonists include, but are not limited to, Enzalutamide, Bicalutamide, Ostarine, Flutamide, Cyproterone acetate, Gugguisterone, Nilutamide, PF998245, (R)-Bicalutamide, and 1,1-Dichloro-2,2-bis(4-chlorophenyl)ethene, ARN-509 and MDV-3100.

In some embodiments, the methods described herein further comprise administering an inhibitor of androgen synthesis to the subject. An exemplary inhibitor of androgen synthesis is Abiraterone acetate.

In some embodiments, the methods described herein further comprise administering a GnRH agonist to the subject. Exemplary GnRH agonists include, but are not limited to, leuprolide, buserelin, histrelin, goserelin and deslorelin.

In some embodiments, the methods described herein further comprise administering a GnRH antagonist to the subject. Exemplary GnRH antagonists include, but are not limited to, cetrorelix, ganirelix, abarelix and degarelix.

B. Chemotherapeutic Agents

In some embodiments, chemotherapy may be administered, optionally in regular cycles. Standard of care chemotherapeutic regimens for patients with prostate cancer include, but are not limited to Docetazel, Cabazitaxel, Mitoxantrone, Estramustine, Doxorubicin, Etoposide, Vinblastine, Paclitaxel, Carboplatin and Vinorelbine. In some embodiments, docetaxel in combination with predisone is administered in combination with the AVPR antagonist described herein.

Chemotherapeutic agents contemplated for use with the methods described herein, include, but are not limited to, erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), bevacizumab (AVASTIN®, Genentech), trastuzumab (HERCEPTIN®, Genentech), pertuzumab (OMNITARG®, rhuMab 2C4, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanam-ine, NOLVADEX®, ISTUBAL®, VALODEX®), doxorubicin (ADRIAMY-CINO), Akti-1/2, HPPD, rapamycin, and lapatinib (TYK-ERB®, Glaxo SmithKline), oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEX®, AstraZeneca), leucovorin (folinic acid), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), capecitabine (XELODA®, Roche), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571

(SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®), alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone), a camptothecin (including the synthetic analog topotecan), bryostatin, callystatin, CC-1065 (including its adozelesin, carzelesin and bizelesin synthetic analogs); cryptophycins (particularly cryptophycin 1 and cryptophycin 8), dolastatin, duocarmycin (including the synthetic analogs, KW-2189 and CBI-TMI); eleutherobin, pancratistatin, a sarcodictyin; spongistatin, nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, calicheamicin gamma1I, calicheamicin omegaI1, dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

C. Radiation Therapy

Radiation and radiotherapeutic agents may also be used in accordance with the methods described herein. Radiation includes, e.g., 7-rays, X-rays, microwaves and UV-irradiation. Radiation may be applied directly to an area of interest by directed delivery of radioisotopes to tumor cells. It is most likely that all of these factors effect a broad range of damage on DNA, on the precursors of DNA, on the replication and repair of DNA, and/or on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

D. Immunotherapeutic Agents

Immunotherapeutics may also be employed for the treatment of cancer. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells. Many tumor markers exist and any of these may be suitable for targeting in the context of the present invention. Exemplary markers expressed in prostate tissues include, but are not limited to, prostate-specific antigen (PSA), prostate-specific membrane antigen (PSMA), prostatic acid phosphatase (PAP), prostate stem cell antigen (PSCA), T cell receptor gamma alternate reading frame protein (TARP), transient receptor potential (trp)-p8 and six-transmembrane epithelial antigen of the prostate 1 (STEAP1).

E. Regulators of Programmed Cell Death

Apoptosis, or programmed cell death, is an essential process in cancer therapy (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Members of the Bcl-2 that function to promote cell death such as, Bax, Bak, Bik, Bim, Bid, Bad and Harakiri, are contemplated for use in combination the AVPR antagonist described herein.

F. Surgery

It is further contemplated that a surgical procedure may be employed. Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an AVPR antagonist. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

G. Other Agents

It is contemplated that other agents may be used in combination with the methods described herein to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In other embodiments, cytostatic or differentiation agents can be used in combination with the invention to improve the anti-hyperproliferative efficacy of the treatments. Inhibitors of cell adhesion are also contemplated to improve the efficacy of treatment. Examples of cell adhesion inhibitors are focal adhesion kinase (FAKs) inhibitors and Lovastatin.

Pharmaceutical Composition, Dosage and Routes of Administration

Compositions comprising an AVPR antagonist described herein are also provided. The compositions contain, for example, an AVPR antagonist and, optionally, pharmaceutically acceptable carrier. The pharmaceutical compositions used in the foregoing methods preferably are sterile and contain an AVPR antagonist for producing the desired response in a unit of weight or volume suitable for administration to a patient. The pharmaceutical compositions may contain suitable buffering agents, including: acetic acid in a salt; citric acid in a salt; boric acid in a salt; and phosphoric acid in a salt.

When administered, the therapeutic compositions are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term denotes an organic or inorganic ingredient, natural or synthetic, with which the active ingredient is combined to facilitate the application. The components of the pharmaceutical compositions also are capable of being co-mingled with the AVPR antagonist, and with each other, in a manner such that there is no interaction which would substantially impair the desired pharmaceutical efficacy.

The AVPR antagonist (or a composition comprising the AVPR antagonist) can be administered by any conventional route, including injection or by gradual infusion over time. The administration may, for example, be oral, intravenous, intratumoral, intraperitoneal, intramuscular, intracavity, subcutaneous, or transdermal. In some embodiments, the AVPR antagonist is administered by oral gavage. When using antisense preparations of the invention, slow intravenous administration is preferred.

The AVPR antagonist (or a composition comprising the AVPR antagonist) is administered in effective amounts. An "effective amount" with respect to an AVPR antagonist according to the teachings herein is that amount of an AVPR antagonist composition that alone, or together with further doses, produces the desired response, e.g., treats prostate cancer or decreases the proliferation of prostate cancer cells. In the case of treating a particular disease or condition characterized by expression of one or more cancer-testis polypeptides, such as cancer, the desired response is inhibiting the progression of the disease. This may involve slowing the progression of the disease temporarily, although more preferably, it involves halting the progression of the disease permanently. Disease progression and cancer cell death can be monitored by routine methods. In various aspects, administration of the AVPR antagonist delays onset or prevents the onset of prostate cancer (e.g., recurrence of the prostate cancer following androgen deprivation. In various embodiments, administration of the AVPR antagonist mediates a reduction in tumor size, such as a reduction in primary tumor volume. Optionally, the method described herein reduces tumor size by at least 1%, 3%, 5%, 10% or more. Alternatively or in addition, the method described herein reduces tumor burden (by, for example, 1%, 3%, 5%, 10% or more); slows, delays, or prevents metastasis; results in a reduction in prostate specific antigen levels in the blood (by, for example, 1%, 3%, 5%, 10% or more); or improves prostate cancer grading used by clinicians (e.g., Gleason score). In various embodiments, the methods described herein decreases prostate cancer cell proliferation by at least 1%, 3%, 5%, 10% or more.

Amounts of AVPR antagonist will depend on the severity of the condition, the individual patient parameters including age, physical condition, size and weight, the duration of the treatment, the nature of concurrent therapy (if any), the specific route of administration and like factors within the knowledge and expertise of the health practitioner. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A cycle may involve one dose, after which several days or weeks without treatment ensues for normal tissues to recover from the drug's side effects. Doses may be given several days in a row, or every other day for several days, followed by a period of rest. If more than one drug is used, the treatment plan will specify how often and exactly when each drug should be given. The number of cycles a person receives may be determined before treatment starts (based on the type and stage of cancer) or may be flexible, in order to take into account how quickly the tumor is shrinking. Certain serious side effects may also require doctors to adjust chemotherapy plans to allow the patient time to recover.

The doses of AVPR antagonist compositions administered to a subject can be chosen in accordance with different parameters, such as the mode of administration used. In the event that a response in a subject is insufficient at the initial doses applied, higher doses (or effectively higher doses by a different, more localized delivery route) may be employed to the extent that patient tolerance permits.

In general, doses of AVPR antagonist are formulated and administered in doses between 0.5 mg/ml to about 500 mg/ml, according to any standard procedure in the art. In some embodiments, the AVPR antagonist is formulated and administered at a dose ranging from 0.5 mg/ml to about 200 mg/ml, or about 1 mg/ml to about 100 mg/ml, or about 1 mg/ml to about 50 mg/ml. In some embodiments, the AVPR antagonist is formulated and administered at a dose of about 0.5 mg/ml or about 1 mg/ml, or about 5 mg/ml, or about 10 mg/ml, or about 20 mg/ml, or about 30 mg/ml, or about 40 mg/ml, or about 50 mg/ml, or about 60 mg/ml, or about 70 mg/ml, or about 80 mg/ml, or about 90 mg/ml, or about 100 mg/ml, or about 150 mg/ml, or about 200 mg/ml, or about 250 mg/ml, or about 300 mg/ml, or about 350 mg/ml, or about 400 mg/ml, or about 450 mg/ml or about 500 mg/ml. Administration of AVPR antagonist compositions to mammals other than humans, e.g., for testing purposes or veterinary therapeutic purposes, is carried out under substantially the same conditions as described above.

The pharmaceutical compositions also may contain, optionally, suitable preservatives, such as benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, and lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases, and the like.

All publications and patents mentioned herein are hereby incorporated by reference in their entirety as if each individual publication or patent was specifically and individually indicated to be incorporated by reference. In case of conflict, the present application, including any definitions herein, will control.

The invention may be more readily understood by reference to the following example, which are given to illustrate the invention and not in any way to limit its scope.

EXAMPLES

Figure 2:
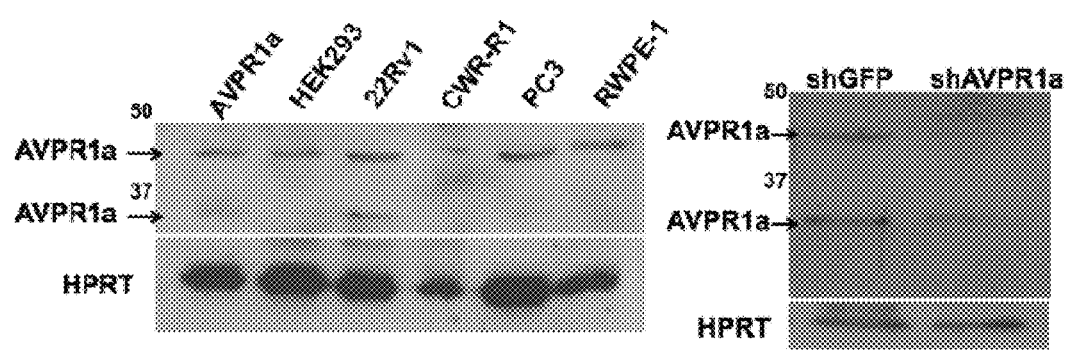
FIG. 2. Arginine Vasopressin Receptor 1a (AVPR1a) is present in prostate cancer cells. 22Rv1 stably depleted of AVPR1a with a receptor subtype specific shAVPR1a or stably expressing shGFP (control) lysates were probed for AVPR1a and HPRT (loading control). Both full length AVPR1a and its major proteolytic product are indicated.
Figure 3A:
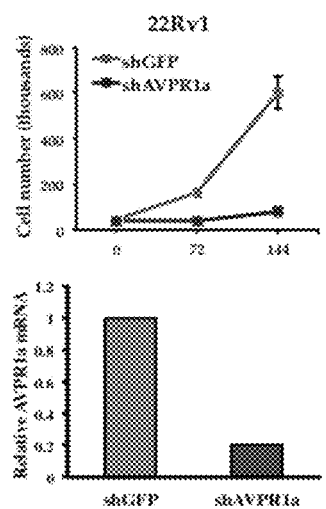
FIGS. 3A-3D. Depletion of AVPR1a decreases aggressive prostate cancer cell proliferation. Representative growth curves (of three independent experiments performed in triplicate) for each cell line stably expressing shGFP (control) or shAVPR1a are shown. Live cells (trypan blue exclusion) were counted at the indicated times (hr). Significant differences ($p<0.05$) in proliferation between shGFP and shAVPR1a-transduced cells occurred by 48-72 hr in CRPC (A-C) but not in normal prostate epithelial cells, RWPE-1 (D). Lower panels quantify AVPR1a mRNA depletion by shRNA in each cell line.
Figure 3B:
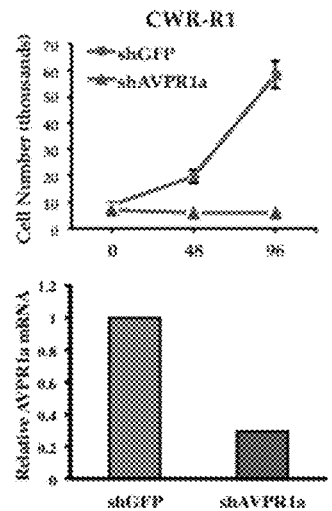
Figure 3C:
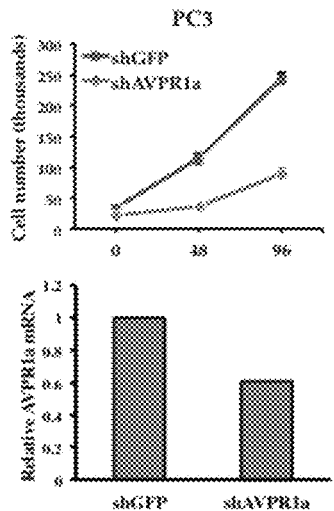
Figure 3D:
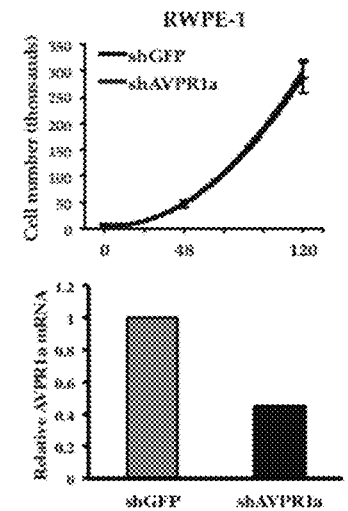
Figure 4A:
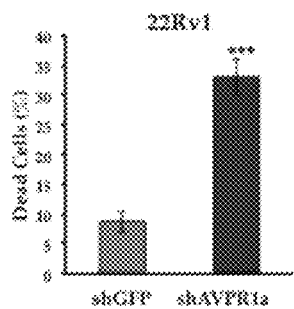
FIGS. 4A-4E. Depletion of AVPR1a promotes death of aggressive prostate cancer cells. (A) 22Rv1, (B) CWR-R1, (C) PC3 or (D) RWPE-1 cells stably expressing either plk0.1-shGFP or -shAVPR1a were plated and grown as in FIG. 3. Adherent and floating cells were harvested and cells that stained with trypan blue or that excluded stain were counted. Data represent three independent experiments performed in triplicate. Significance was determined using a Student's t-test comparing to shGFP controls (***, $p<0.001$). (E) Cell lysates were immunoblotted with antibodies that recognize cleaved PARP, cyclin A, and actin.
Figure 4B:
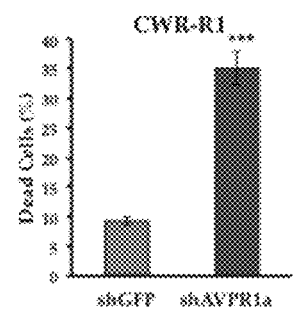
Figure 4C:
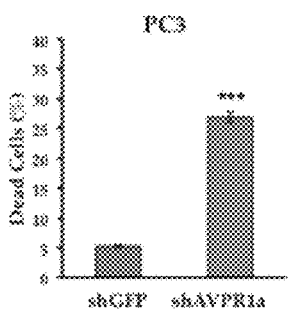
Figure 4D:
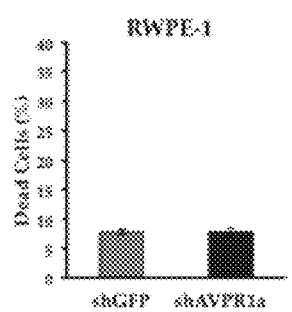

Example 1—Arginine Vasopressin Receptor 1a (AVPR1a) is Present in Prostate Cancer Cells AVPR1a was identified during efforts to define the genes responsible for CRPC growth and survival. Both Vav3 (a coactivator of full length AR and AR splice variants) as well as the prevalent and clinically relevant AR splice variant AR3 (AR-V7) are essential for proliferation and survival of human CRPC cell lines including 22Rv1 (21). Gene expression profiling was performed by microarray of 22Rv1 cells in which Vav3 or AR3 were inducibly depleted. Three independent 22Rv1 cell isolates were derived for each of the following shRNAs (shGFP, shAR3, and shVav3) for a total of 9 independent cell derivatives. Depletion of AR3 or Vav3 but not the GFP control resulted in significant reduction of arginine vasopressin receptor 1a (AVPR1a) mRNA levels (false discovery rate of 5%, cutoff of ±1.5). AVPR1a protein was expressed in 22Rv1 cells (FIG. 2) and in other human CRPC lines including PC3 as well as to a lesser extent in RWPE-1 (normal human prostate epithelial cells) (data not shown). Most endogenous GPCRs are exceedingly difficult to detect using immunologic reagents (due in part to low abundance of these proteins). Nevertheless, decreased AVPR1a protein was detected in cells expressing a selective shRNA (SEQ ID NO: 2-GGT ATG TGG AAG GAC TCG CCT AAA TCT TC) to AVPR1a (FIG. 2). In terms of mRNA levels, AVPR1a mRNA was highest in 22Rv1 and lowest in the normal RWPE1 cells. While PC3 cells do not express full length AR or AR splice variants, AVPR1a is expressed suggesting that there are additional mechanisms to maintain AVPR1a expression in CRPC.

shRNA-mediated depletion of AVPR1a resulted in decreased cell proliferation (FIG. 3A-C) and increased cell death (FIG. 4A-C) of multiple aggressive human PC cell lines: PC3, 22Rv1 and CWR-R1 but not the normal human prostate epithelial RWPE1 cells (FIG. 3D&4D). The same results were obtained with a second distinct shAVPR1a construct (SEQ ID NO: 3: TCTCCATGATCGAGGTGAACAATGTCACC) (data not shown).

Figure 4E:
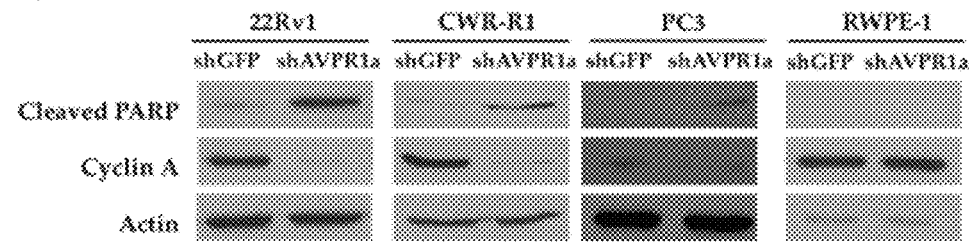
Figure 5:
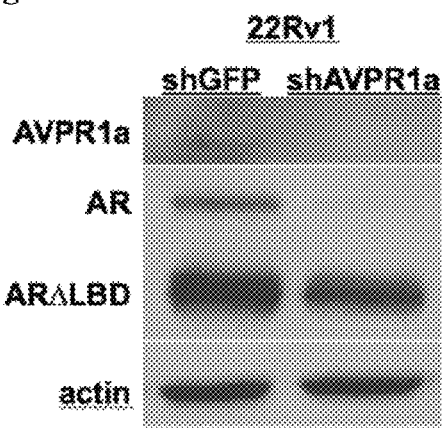
FIG. 5. AVPR1a knock down results in down-regulation of androgen receptor (AR) and AR splice variant expression in human prostate cancer cells. 22Rv1 stably expressing shGFP or shAVPR1a were immunoblotted with the indicated antibodies. ARdeltaLBD refers to C-terminally truncated AR splice variants such as AR3.
Figure 6:
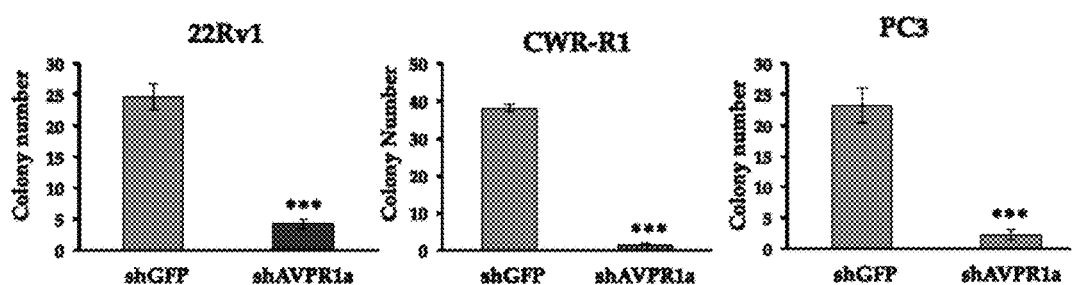
FIG. 6. AVPR1a is necessary for anchorage independent growth of human prostate cancer cells. The growth in soft agar of 22Rv1, CWR-R1 or PC3 cells stably expressing the indicated shRNA vectors was assessed. Average colony number per plate±SEM is plotted. Data represent two independent experiments performed in triplicate. Significance was determined using a Student's t-test comparing to shGFP controls (***, $p<0.001$).

Poly ADP ribose polymerase (PARP) cleavage, indicative of apoptosis, was also observed in AVPR1a-depleted PC cells but not in RWPE1 cells (FIG. 4E). AVPR1a depletion decreased G1 to S cell cycle progression in PC as indicated by decreased levels of Cyclin A (FIG. 4E). Interestingly, depletion of AVPR1a in the CRPC 22Rv1 cell line resulted in decreased levels of full length AR and AR splice variants (FIG. 5). This finding is significant as AR splice variants are a proposed mechanism of resistance to drugs that target full length AR including the newer agents, abiraterone and enzalutamide (6,7). Thus, targeting AVPR1a may be a strategy to overcome therapeutic resistance to these next generation drugs. Depletion of AVPR1a decreased the transformed phenotype of the three PC cell lines as shown by inhibition of anchorage independent growth in soft agar and resistance to anoikis (FIG. 6). Normal RWPE1 cells do not grow in soft agar and were therefore not examined. All findings were reproduced with a 2nd distinct shAVPR1a construct (data not shown). These data demonstrate that inhibition of AVPR1a (e.g., via downregulation of AVPR expression using oligonucleotide antagonists) is useful in the treatment of CRPC.

Example 2—Relcovaptan Promoted Prostate Cancer Cell Apoptosis

We will test the effects of AVPR1a depletion (shRNA) and antagonism [Relcovaptan (SR49059)], in three clinical settings in which new treatments are most critically needed: established CRPC tumors, the window during which androgen dependent tumors progress to CRPC under androgen deprivation therapy and in metastatic disease.

AR-expressing human PC cell lines, 22Rv1, CWR-R1 and VCaP are suitable for evaluating the efficacy of AVPR antagonists in the context of the invention as AR is expressed in the majority of CRPC. These cell lines have distinct genetic features that model PC in men [Table 1, (23,24)].

| Cell Line | AR full length | AR splice variant | PTEN status | CRPC | TMPRSS2/ ERG fusion |
|---|---|---|---|---|---|
| VCaP | WT (amplified) | negligible* | WT | No** | Yes |
| 22Rv1 | functional full length mutant | Yes | WT | Yes | No |
| CWR-R1 | functional full length mutant | Yes | WT | Yes | No |
| PC3 & PC3-ML | null | null | mutant | Yes | No |

Figure 11:
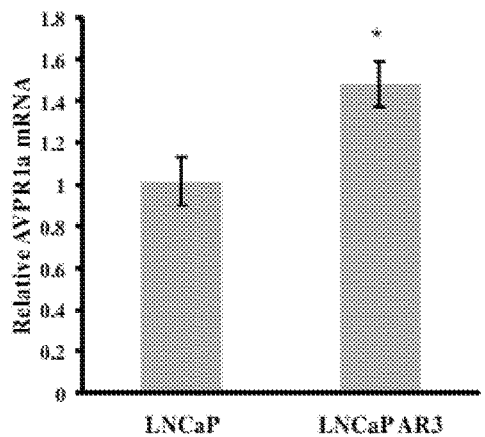
FIG. 11 shows that AR3/AR-V7 upregulated AVPR1a expression in a human prostate cancer cell line.

*AR splice variants are expressed following castration (21, 29)
**progresses to CRPC in vivo The 22Rv1 and CWR-R1 lines were derived by performing serial xenografts of human PC cells in castrated immunocompromised mice to select for CRPC. 22Rv1 and CWR-R1 have key features that model human CRPC tumors including expression of full length mutant AR and AR splice variants. AR somatic mutations and constitutively active AR splice variants are expressed in a substantial number of CRPC cases (3-7). The VCaP line, expresses wild type and amplified AR, and are androgen dependent for growth (25). VCaP cells readily progress to CRPC in vivo following androgen deprivation (21,26,27). These cells also express the TMPRSS2/ERG fusion, a gene rearrangement that occurs in approximately half of primary human PC tumors (28). In addition, VCaP cells express constitutively active AR splice variants following progression to CRPC (21,29). VCaP, 22Rv1 and CWR-R1 cell lines are PTEN WT similar to approximately 50% PCs (30). Since Relcovaptan inhibits proliferation and promotes cell death of the PC3 human PC cell line, which expresses inactive PTEN mutants (23), this treatment strategy appears to be effective regardless of PI3K signaling status. PC3-ML is a metastatic derivative of PC3 cells (31). PC3-ML is valuable for examining the effects of AVPR1a antagonism on tumor metastasis in an orthotopic xenograft model (FIG. 11).

Figure 7A:
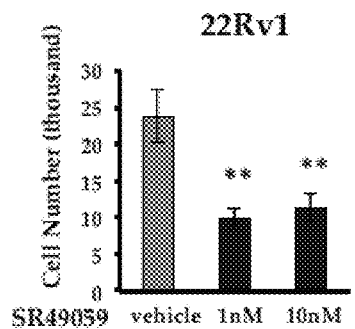
FIGS. 7A-7I. Pharmacologic blockade of AVPR1a decreases human prostate cancer cell but not normal prostate epithelial cell proliferation and selectively kills human prostate cancer cells. (A) 22Rv1, (B) CWR-R1, (C) PC3, and (D) RWPE-1 cells were treated with vehicle or SR49059 at the indicated concentrations and harvested five days post treatment. A representative experiment (of four) was performed in triplicate and data are plotted as cell number (thousands) ±SD. Significance was determined using a Student's t-test comparing to vehicle controls (, $p<0.01$; *, $p<0.001$). (E) 22Rv1, (F) CWR-R1, (G) PC3 or (H) RWPE-1 cells were plated and grown as described above. Adherent and floating cells were harvested and cells that stained with trypan blue or that excluded stain were counted. A representative experiment (of four) was performed in triplicate. Significance was determined using a Student's t-test comparing to vehicle controls (, $p<0.01$; *, $p<0.001$). (I) Lysates from cells in (A)-(D) were immunoblotted with antibodies that recognize cleaved PARP and actin.
Figure 7B:
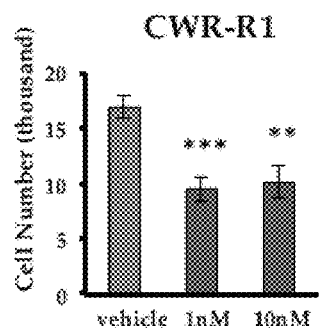
Figure 7C:
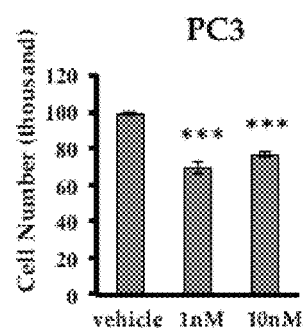
Figure 7D:
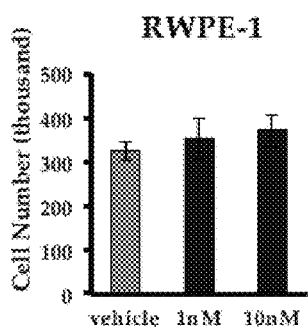
Figure 7E:
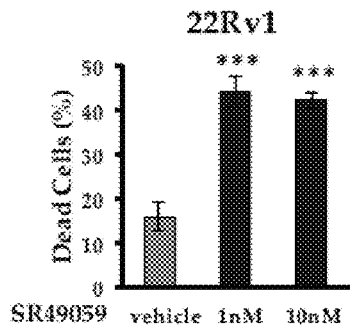
Figure 7F:
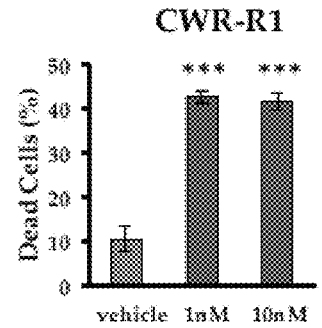
Figure 7G:
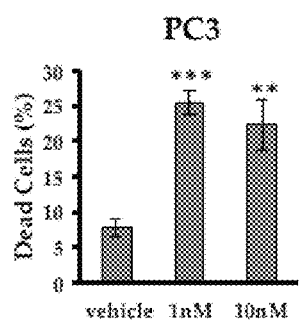
Figure 7H:
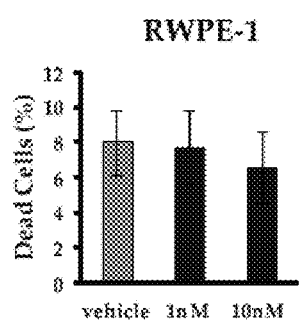
Figure 7I:
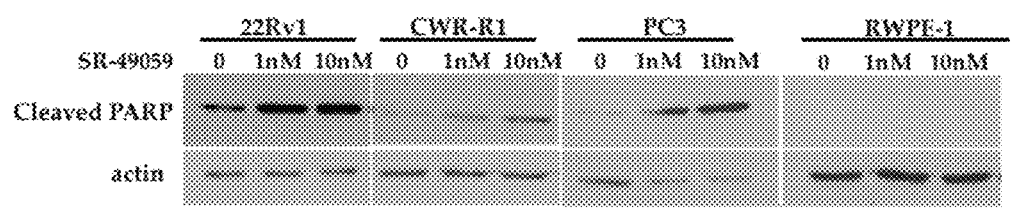

Since AVPR1a is important for the growth and survival of PC cells, we tested SR 49059 (Relcovaptan), a drug that specifically targets AVPR1a (2) was evaluated in the AR-expressing PC cells. Relcovaptan inhibited proliferation and promoted CRPC cell death in PC3, 22Rv1 and CWR-R1 at low nanomolar concentrations (FIG. 7A-C, E-G). Relcovaptan inhibited growth inhibition and caused cell death (approx. 20%) in androgen dependent LNCaP cells (data not shown). In contrast, Relcovaptan (1-10 nM) had no effect on RWPE1 cell proliferation or survival (FIG. 7 D,H). Doses as high as 10 μM did not promote RWPE1 cell death (data not shown). Relcovaptan treatment also resulted in cleavage of PARP in PC but not normal prostate cells (FIG. 7I). Relcovaptan treatment promoted PC cell apoptosis but did not affect normal prostate epithelial cells.

Figure 8:
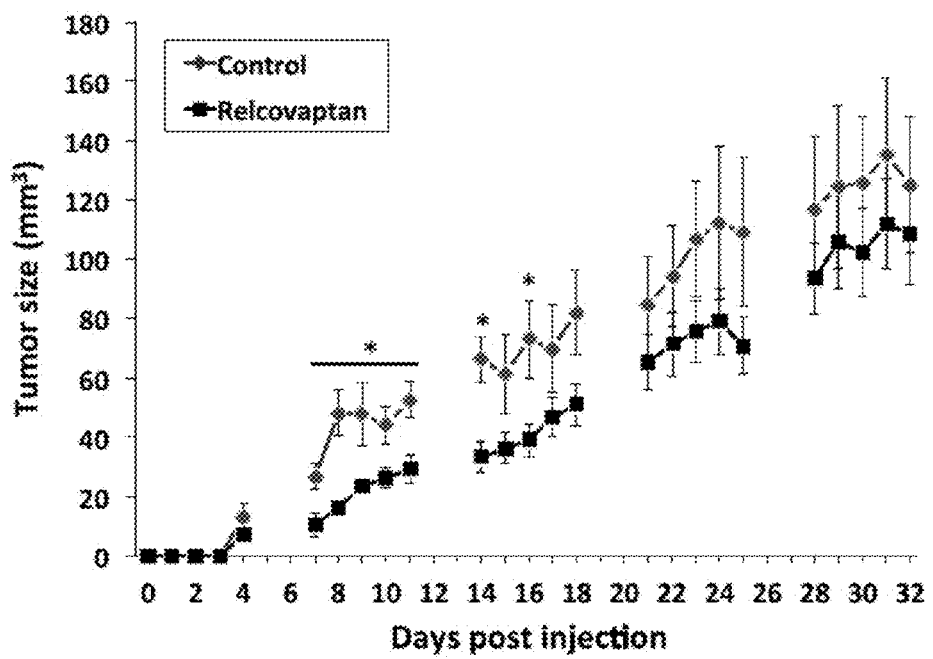
FIG. 8. Relcovaptan (SR49059) decreases CRPC in vivo growth at early time points. 22RV1 cells ($2\times10^6$) resuspended in BD Matrigel were injected into both hind flanks of castrated nude mice (n=8). The following day PBS (vehicle) (n=4) or 2.5 mg/kg Relcovaptan (TOCRIS) (n=4) was administered via IP injection once daily, five times a week. Top graph, once palpable, tumor size was measured five days per week. Significance was determined using a Student's t-test comparing to vehicle controls (* $p<0.05$). Lower graph, mice were weighed five days per week. There were also no observable differences in general health or behavior in the control vs. Relcovaptan-treated mice indicating lack of toxicity of Relcovaptan.
Figure 8:
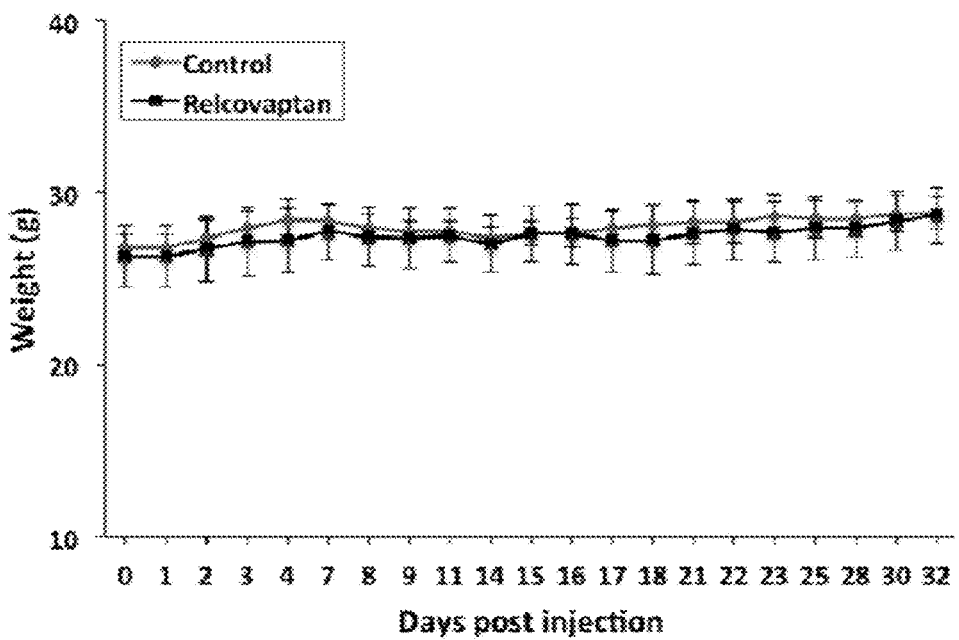
Figure 9A:
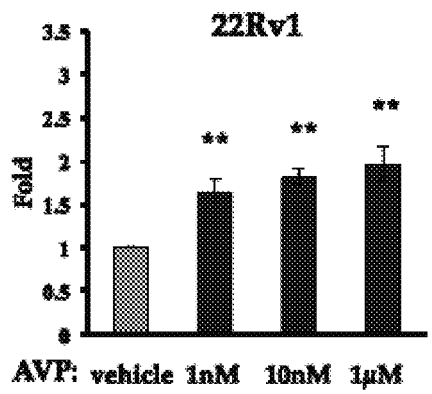
FIG. 9A-9D. Arginine vasopressin (AVP) stimulates castration resistant prostate cancer cell proliferation. (A) 22Rv1, (B) CWR-R1, (C) PC3, or (D) RWPE-1 cells were plated at 10,000 cells/well in 24 well dishes and then treated with vehicle or arginine vasopressin (AVP) at the indicated concentrations the following day. Media were changed every day. Cells were harvested six days post treatment. Data represent four experiments performed in triplicate and are plotted as fold (treatment/vehicle)±SEM. Significance was determined using a Student's t-test comparing to vehicle controls (**, $p<0.01$).
Figure 9B:
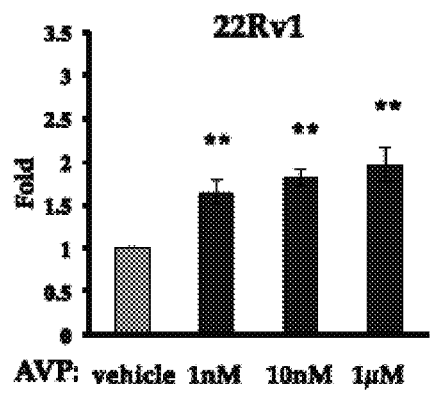
Figure 9C:
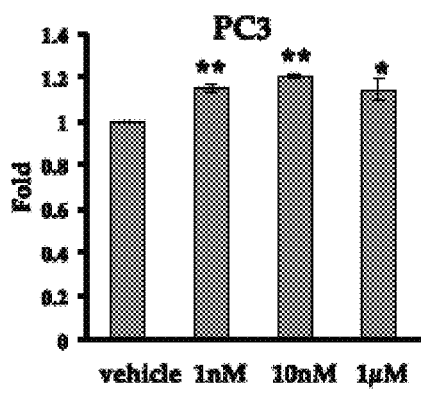
Figure 9D:
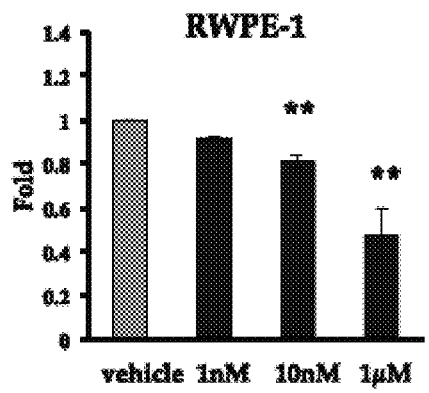

Relcovaptan was also tested in vivo in a small pilot xenograft experiment (FIG. 8). Following establishment of 22Rv1 xenografts in castrated nude mice, Relcovaptan or vehicle was administered IP, 5 times per week (four mice per group (bearing bilateral tumors). The experiments showed significantly decreased tumor growth at early time points (FIG. 8, upper graph). The mice showed no adverse effects from the drug. There were no significant differences in weight gain between controls and treated animals (FIG. 8, lower graph). Mice receiving drug showed no difference in general health and well-being as assessed by behavior, appetite, skin and GI function.

Figure 10:
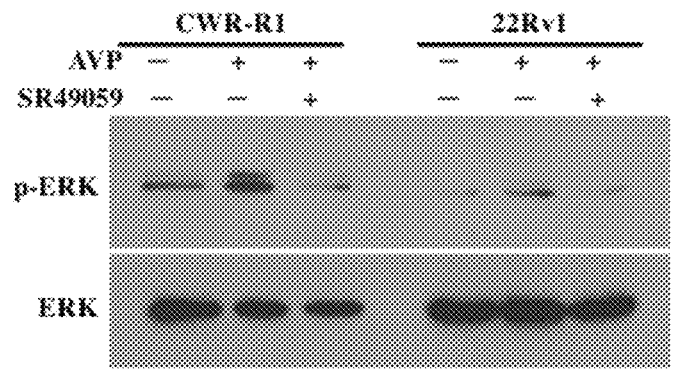
FIG. 10. Arginine vasopressin (AVP) stimulates ERK1/2 phosphorylation. 22Rv1 or CWR-R1 cells were grown in FBS-free media for 48 hours and then treated with 1 nM AVP plus/minus 1 nM Relcovaptan (SR49059) for 25 min. Lysates were immunoblotted for phospho-ERK1/2 and total ERK1/2.

To demonstrate further the significance of AVPR1a in human PC, the ability of arginine vasopressin (AVP), to stimulate growth of CRPC was tested. 1 nM AVP caused increased PC cell proliferation but did not stimulate growth of normal RWPE1 prostate epithelial cells (FIG. 9). Decreased proliferation of RWPE-1 at higher AVP doses may be due to activation of type V2 receptors (22). FIG. 10 shows that AVP activated ERK 1/2 and that Relcovaptan inhibited this phosphorylation of ERK.

Example 3—Assess the Effectiveness of AVPR1a Depletion and AVPR1a Antagonism in Difference Clinical Setting in Two Independent Xenograft Models of Castration Resistant Prostate Cancer A. 22Rv1, a Human CRPC Line.

22Rv1 xenografts in castrated nu/nu mice have been described (26). Mice lack the capacity to synthesize adrenal androgens and therefore castration is an effective method of eliminating the vast majority of androgens (33). These aggressive PC cells form tumors at a take rate of over 95% in castrated mice (26). Optionally, mice are randomized when castration resistant tumors reach 250 mm$^3$ (approx. 3 weeks) and treatment (drug or vehicle control) is initiated. Drug or vehicle control is injected into the peritoneal cavity (IP). While Relcovaptan is orally available, IP injections ensure more accurate dosing. The antagonist, (e.g., Relcovaptan) is given 5 days per week at a dose of 2.5 mg/kg throughout the remainder of the experiment (34). These doses result in comparable drug levels as used in human studies (17,35). Similar experiments can be conducted using 22Rv1 cells stably transfected with a tetracycline-regulated shRNA targeting AVPR1a (or a control shRNA). For these experiments, doxycycline is administered via the drinking water following the same time schedule as for Relcovaptan. In both experiments, tumor volumes are assessed at least twice weekly with calipers and calculated using the formula length×width×height×0.52. Mice are weighed weekly and blood taken biweekly and at sacrifice to determine circulating PSA using an enzyme-linked immunosorbent assay as we have described previously (26,27,36). Tumors are permitted to grow for 5-6 weeks or until tumors reach 1000 mm$^3$. Tumors are excised aseptically, weighed and apportioned for fixation, cell line generation and for quick freezing for use in RNA and biochemical experiments. Some freshly excised tumor tissue is immediately examined for AVPR1a signaling (phospho- and total ERK1/2, phospho and total p90RSK). Tumor lysates are immunoblotted for AVPR1a, AR (full length and splice variants), cyclin A, cleaved PARP, cleaved caspase 3. Evaluation of these proteins provide data on the effects of an antagonist (e.g., Relcovaptan) on its target receptor as well as on cell cycle and apoptosis. Some tumor tissue is fixed in buffered formalin and embedded in paraffin for immunohistochemistry (Ki67, TUNEL assay). These analyses provide an indication of proliferation and apoptosis. For the experiments using 22Rv1/shAVPR1a cells, AVPR1a is examined by RT qPCR to determine extent of AVPR1a knock down in the late stage tumors. Some tumor tissue may be reserved for H&E staining for diagnostic pathology.

B. VCaP, a Model of Androgen Dependent Human Prostate Cancer that Progresses to Castration Resistance In Vivo VCaP cells model in vivo progression to castration-resistance and are suitable to test drug efficacy in this scenario (26). VCaP xenografts are allowed to grow to approximately 250 mm$^3$ in intact mice (typically 6 weeks). Mice are castrated, which is accompanied by a 3-4 week regression/plateau in tumor growth. After this period, tumors resume robust growth indicative of castration resistance. Castration resistance can be defined as the time at which tumor volume is 50% greater than that observed at time of castration. Thus, antagonist (e.g., Relcovaptan) or vehicle treatment of randomized mice are initiated when tumors reach approximately 375 mm$^3$ in the castrated animals. As above, Relcovaptan/vehicle s given five times per week (2.5 mg/kg IP). Tumor volume is evaluated twice a week and mouse weight is measured weekly. Mice are sacrificed when tumors reach 1000 mm$^3$ or 6-8 weeks after the initiation of drug/vehicle treatment.

Similar experiments may be conducted using VCaP cells stably expressing tetracycline regulated shAVPR1a or control shRNA. Mice are castrated and given doxycycline via their drinking water using the same time frame as for the antagonist.

Together, the materials and methods described in this Example determine whether depletion of AVPR1a or antagonism of AVPR1a decreases growth of established CRPC tumors in two human PC models.

C. Effectiveness of AVPR1a Depletion and AVPR1a Antagonism on Prolonging the Time to Castrate Resistance Progression in a Xenograft Model of Human Prostate Cancer.

Since VCaP cells reproducibly progress to castration resistance in xenograft models, this is useful cell line to test the effects of AVPR1a depletion and AVPR1a antagonism on the durability of androgen deprivation therapy. These experiments will be conducted as described above in part B of this Example except that antagonist/vehicle or doxycycline is initiated at the time of castration. Tumor growth is followed for 5-6 weeks after castration and initiation of drug therapy. Circulating PSA will be monitored and tumors analyzed as described above.

An alternative approach to subcutaneously grown xenografts is to use orthotopic xenografts, which better represent the prostate tumor microenvironment and permit analysis of metastasis. Subcutaneous xenografts may provide more consistent progression to castration resistance in the xenograft models described above and are more easily monitored than in an orthotopic setting. The materials and methods described herein will provide a robust test of drug effectiveness and AVPR1a knock down in the two important clinical settings (established CRPC and progression to CRPC).

Example 4—AVPR1a Depletion and AVPR1a Antagonism in In Vitro and In Vivo Metastatic Models of Human PC A. Analysis of AVPR1a Depletion and Antagonism on Metastatic Properties In Vitro Examination of AVPR1a mRNA levels in two independent datasets showed that AVPR1a is upregulated in PC metastases versus primary site tumors (FIG. 1) consistent with a possible role of this receptor in metastatic processes. AVPR1a knock down and inhibition on invasion and migration can be examined in vitro and on metastasis in vivo using orthotopic xenografts. AVPR1a depletion (using tetracycline regulated shAVPR1a) and small molecule or antibody effects on metastatic processes in 22Rv1, CWR-R1 and PC3-ML cell lines can be evaluated by migration and Matrigel invasion assays (38). Experiments can be conducted at time points in the 4-24 hr range.

Migration is assessed using e.g., a Boyden chamber assay. This assay utilizes a 24-well cell culture dish with porous inserts. Cells are serum starved overnight and then pre-treated with vehicle (DMSO) or antagonist (e.g., Relcovaptan) or doxycycline. 5×10$^4$ cells are seeded in the top of the insert, and medium containing 10% FBS is used as a chemoattractant at the bottom of the chamber. Migratory cells travel through the pores and into the bottom of the chamber where they are fixed, stained with crystal violet and counted. Invasion potential is evaluated using e.g., a Matrigel Invasion assay. This assay is similar to the Boyden chamber assay described above, except the porous cell culture inserts are coated in Matrigel. Matrigel mimics components of the basement membrane, and cells capable of degrading Matrigel have potential to leave the primary tumor site and metastasize.

Cellular adhesion is examined using a Millipore ECM colorimetric cell adhesion array kit. Cells are cultured for 24-72 hours in wells coated with different extracellular adhesion proteins such as collagens, fibronectin, laminin, tenascin, and vitronectin. Cells adhering to these substrates are stained and quantified by spectroscopy. Cells are treated with vehicle (DMSO) or antagonist/doxycycline and their adhesion potential evaluated. Adhesion potential is determined by immunoblotting for E-cadherin. E-cadherin is a cell surface adhesion molecule that is downregulated during the epithelial-to-mesenchymal transition (EMT), an important stage in metastasis. Cells are treated with vehicle (DMSO) or antagonist (or doxycycline for AVPR1a depletion experiments) for 24-72 hours, harvested, and immuno-blotted with a monoclonal antibody for E-cadherin. Together, these assays evaluate the effects of AVPR1a depletion and antagonism on cellular processes that impact metastasis.

B. AVPR1a Depletion and Antagonism on Metastasis In Vivo

Orthotopic xenografts reproduce the entire metastatic cascade from loss of cell-cell adhesion, local invasion, intravasation into the bloodstream, survival in the circulation, exit from blood vessels (extravasation) to eventual establishment of tumors at secondary sites. Luciferase-expressing human PC cells are introduced directly into the ventral lobes of prostates of immunocompromised mice. Metastasis reliably occurs in these models and can be evaluated by bioluminescent imaging (39 and FIG. 11). The effects of antagonist (e.g., Relcovaptan) and AVPR1a depletion on metastatic progression and on growth of metastatic lesions are examined by dosing mice after primary tumors have been established (approx. 1-2 weeks in this model) and after metastatic spread (approx. 3-4 weeks).

Orthotopic xenografts in are established in e.g., male nu/nu mice using PC3-ML cells expressing luciferase. Primary tumor formation and metastasis are examined with an IVIS SPECTRUM instrument. A tetracycline regulated shAVPR1a is optionally introduced into PC3-ML Luc cells for parallel AVPR1a depletion studies.

Generation of orthotopic xenografts is achieved through open abdominal surgery with cell injection into the ventral lobe of the mouse prostate. Mice (after attrition, n=16 per group with tumors) are imaged weekly beginning approximately 1 week after tumor cell injection (39,40). Mice are imaged using the UMMSM Oncogenomics Core Caliper/Xenogen IVIS SPECTRUM System equipped with Living Image software 4.0. Antagonist treatment is initiated after primary tumors have formed but prior to metastasis. To image metastatic sites, the primary tumor is optionally shielded and imaging is conducted for longer times. At the time of sacrifice, mice are injected with luciferin and the prostate/seminal vesicles removed. Following removal of the prostate/seminal vesicles, the mice are imaged to detect distal metastasis. The prostates and seminal vesicles are imaged ex vivo to quantify primary (prostate) tumors and local invasion into the seminal vesicles. Other internal organs (e.g. lung, liver, spleen) may be excised and imaged ex vivo.

Example 5—Arginine Vasopressin Receptor 1a (AVPR1a) is a Co-Target of Androgen Receptor Variant AR-V7 (Also Known as AR3) and the Androgen Receptor Coactivator, Vav3

Androgen receptor (AR) signaling is maintained in castration resistant prostate cancer (CRPC), which provides an explanation for the efficacy of drugs such as abiraterone and enzalutamide that inhibit androgen production or target AR directly, respectively. Unfortunately, up-regulation of constitutively active AR variants (e.g. AR-V7/AR3) often occurs in CRPC and is linked to poor prognosis and abiraterone/enzalutamide resistance. AVPR1a was identified during efforts to define the genes responsible for CRPC growth and survival.

Both Vav3 (a coactivator of full length AR and AR variants) and the prevalent and clinically relevant AR variant AR-V7 (AR3) are essential for proliferation and survival of human CRPC cell lines, including 22Rv1 (Peacock et al. 2012 PMID: 23023561 and unpublished data). Briefly, gene expression profiling by microarray of 22Rv1 cells was performed in which Vav3 or AR-V7 were inducibly depleted. Three independent 22Rv1 cell isolates were derived for each of the following shRNAs:

shGFP
(SEQ ID NO: 5 - GCAAGCTGACCCTGAAGTTCATCTCTTGAATG

AACTTCAGGGTCAGCTTGC), shAR-V7
(SEQ ID NO: 6 - GCAAGCTGACCCTGAAGTTCATTCAAGAGATG

AACTTCAGGGTCAGCTTGC),
and shVav3
(SEQ ID NO: 7 - CCGGGCTTTGTCTAACATAAGACCTCGAGGTC

TTATGTTAGACAAAGCTTTTG)

for a total of nine independent cell derivatives Depletion of AR-V7 or Vav3, but not the GFP control, resulted in significant reduction of AVPR1a mRNA levels (false discovery rate of 5%, cutoff of ±1.5). Thus, AVPR1a is a novel AR-V7 (AR3)- and Vav3-regulated gene. AVPR1a expression was not restricted to AR variant-expressing prostate cancer cells, suggesting that while AVPR1a is a target of AR variants, expression of this gene can be maintained by additional mechanisms.

Example 6—Expression of AR Variant in Androgen Dependent LNCaP Cells Results in Increased AVPR1a mRNA LNCaP cells (human prostate cancer cell line) were transfected with AR-V7 (AR3) or empty vector control and grown in 2% CSS for 48 hours. Reverse transcriptase, real time PCR was performed using Taqman probes for AVPR1a and HPRT 1 (control). Data represent four independent experiments performed in triplicate with AVPR1a mRNA levels for LNCaP cells set at one (relative mRNA levels±SEM). See FIG. 11. These data validate that AVPR1a is regulated by AR-V7 (AR3) in an additional human prostate cancer cell line.

Figure 1B:
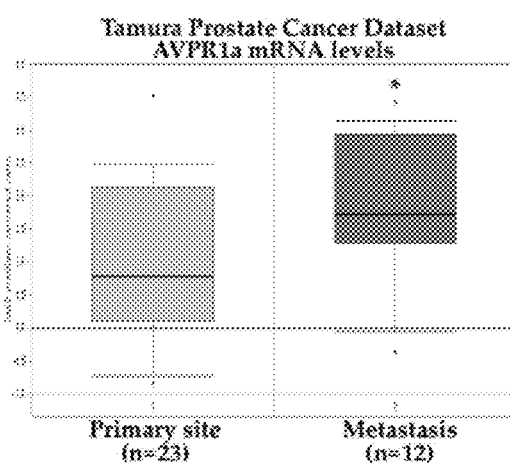
Figure 1C:
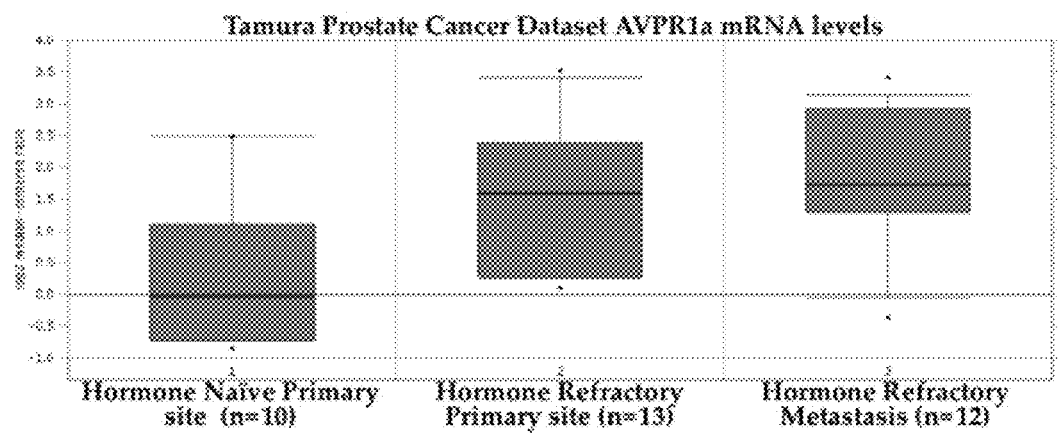

Example 7—AVPR1a is Expressed at Highest Levels in Metastatic Compared to Primary Prostate Cancer (CaP) Sites Utilizing the Oncomine™ database (Compendia Bioscience, Ann Arbor, Mich.), two distinct datasets containing metastatic CRPC human specimens were identified that showed elevations of AVPR1a mRNA in metastatic vs. primary site (prostate) human cancer (4.3-fold increase in Chandran and 1.7 fold in Tamura datasets) (FIGS. 1A and 1B). The metastatic samples from both datasets were castration resistant (obtained from patients whose disease progressed despite androgen deprivation therapy). However, in the Tamura dataset, the primary site cancer specimens were a mix of 13 CRPC and 10 hormone naïve samples (from patients who did not undergo androgen deprivation). Stratification of the primary site (localized) samples shows that AVPR1a is higher in CRPC localized in the prostate compared to hormone naïve primary site tumors (FIG. 1C). These results indicate that AVPR1a is upregulated particularly in advanced human prostate cancer compared to primary site cancer and benign prostate tissues.

Example 8—Depletion of AVPR1a Profoundly Reduced Growth of Castration Resistant Prostate Cancer Cells AVPR1a was depleted using an shRNA (● shAVPR1a, SEQ ID NO: 4-GGTATGTGGAAGGACTCGC- CTAAATCTTCCTCGAGGAAGATTTAGGCGAGTCCTTCCACATACC) in castration resistant cells (CRPC), PC3, 22RV1, LNCaP-abl, C4-2, CWR-R1, and androgen dependent cells, LNCaP, VCaP and non-tumorigenic prostate epithelial RWPE1 cells, followed by live cell counting on the indicated days. (● shGFP served as a control, SEQ ID NO: 5-GCAAGCTGACCCTGAAGTTCATCTCTTGAAT-GAACTTCAGGGTCAGCTTGC A summary of the human prostate cell lines used is provided below in Table 1:

| Cell line | Androgen dependent of CRPC | AR full length/AR Variant expression | TMPRSS2-ERG Fusion |
|---|---|---|---|
| PC3 | CRPC | None | No |
| 22Rv12 | CRPC | +/++ | No |
| LNCaP Abl* | CRPC | +/− | No |
| C4-2* | CRPC | +/− | No |
| CWR-R1 | CRPC | +/− | No |
| LNCaP | Androgen dependent | +/− | No |
| VCaP | Androgen dependent | ++/+# | Yes |
| RWPE1 | Non-tumorigenic prostate epithelial | +/− | No |

Figure 12:
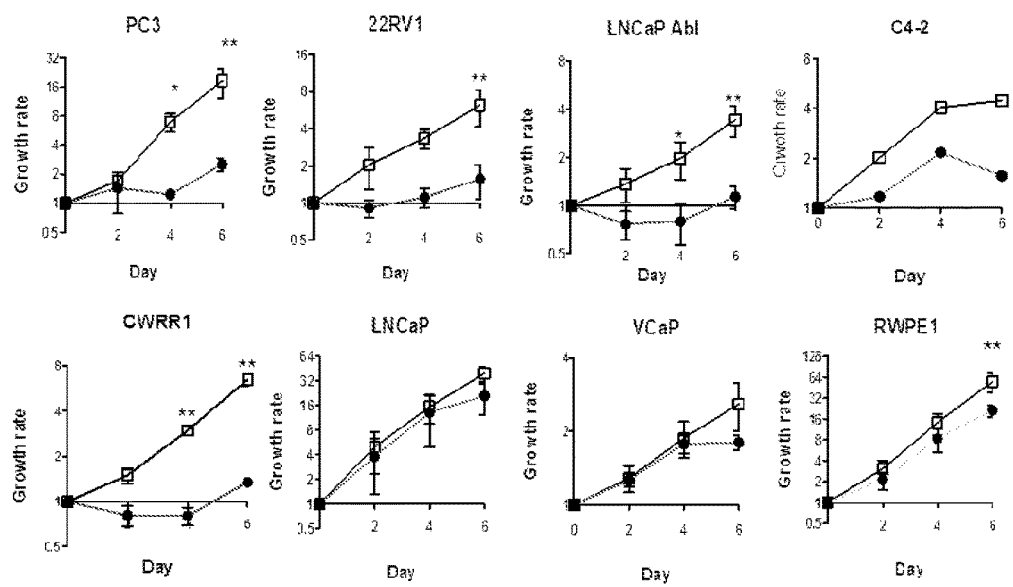
FIG. 12 shows that depletion of AVPR1a significantly reduced growth of castration-resistant prostate cancer (CRPC) cells.

*castration-resistant derivative of LNCaP
AR variant expression increases after androgen deprivation The results are provided in FIG. 12. Data represent three independent experiments performed in triplicate for all cell lines except C4-2, which was done one time in triplicate. Depletion of AVPR1a with a subtype-specific shRNA greatly decreased proliferation of CRPC cells, but had less effect on androgen dependent and normal prostate epithelial cell proliferation. A second distinct AVPR1a shRNA produced similar results (data not shown).

Figure 13:
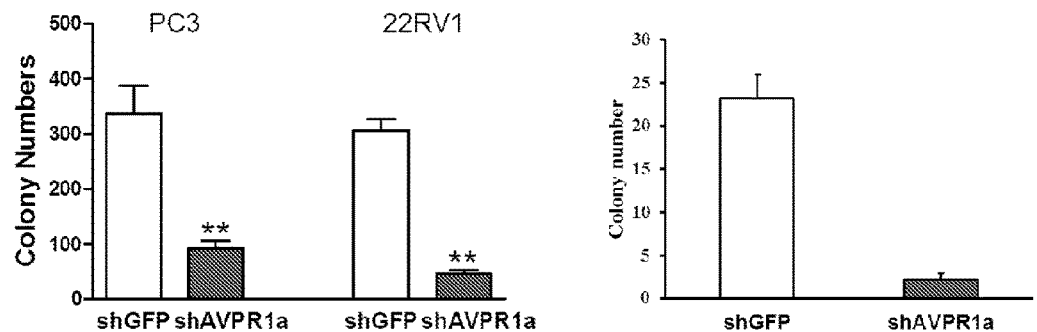
FIG. 13 shows that AVPR1a is critical for advanced prostate cancer anchorage independent growth.

Next, PC3 and 22RV1 cells (CRPC cell lines) in which AVPR1a was depleted (or control shGFP) were cultured in soft agar for three weeks to assess anchorage independent growth (anoikis resistance). Results indicated that depletion of AVPR1a in the cells significantly reduced anchorage independent growth of CRPC cells. See FIG. 13.

Figure 14:
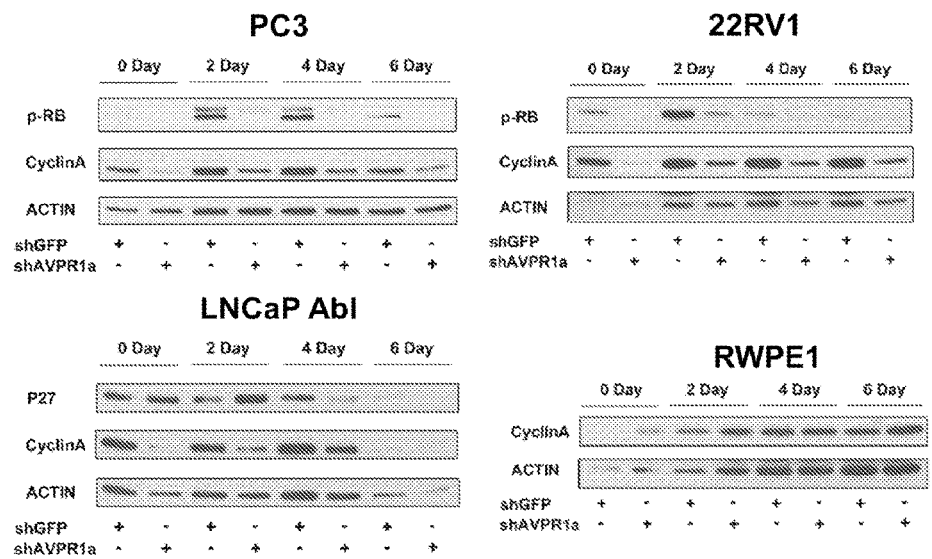
FIG. 14 shows that AVPR1a promotes advanced prostate cancer cycle progression.

Next, Western-blot analysis was performed in PC3, 22Rv1 and LNCaP Abl (CRPC) and RWPE1 (non-tumorigenic prostate epithelial cells) to examine G1/S cell-cycle markers: Cyclin A, p-RB or P27. Consistent with reduced cell proliferation, depletion of AVPR1a resulted in in decreased cyclin A in the CRPC lines but not in the non-tumorigenic RWPE1 cell line. Similarly, depletion of AVPR1a in PC3 and 22Rv1, but not RWPE1 cells, resulted in decreased phosphorylation of the retinoblastoma protein indicative of decreased G1 to S phase progression. See FIG. 14.

Example 9—Arginine Vasopressin Stimulated CRPC Proliferation

Figure 15:
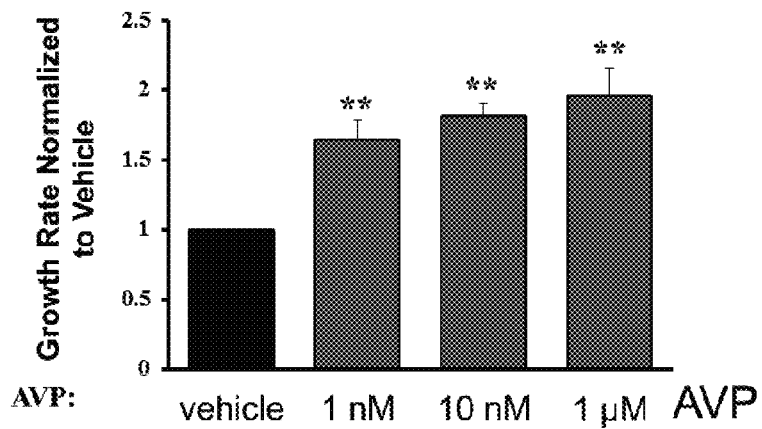
FIG. 15 shows that arginine vasopressin stimulated CRPC proliferation.
Figure 16:
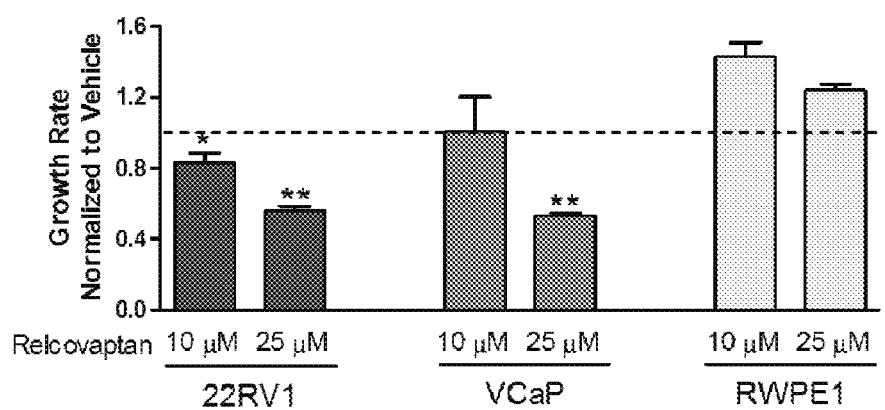
FIG. 16 shows that AVPR1a antagonist Relcovaptan inhibits prostate cancer cell proliferation.

The effect of arginine vasopressin on the proliferation of a castration-resistant prostate cancer cell line (i.e., 22Rv1) was evaluated. Briefly, 22RV1 cells were treated with 1 nM, 10 nM or 1 µM arginine vasopressin (AVP) for six days followed by live cell counting. Results show that arginine vasopressin stimulated CRPC proliferation. See FIG. 15. AVP did not stimulate RWPE1 cell proliferation (data not shown).

Figure 17:
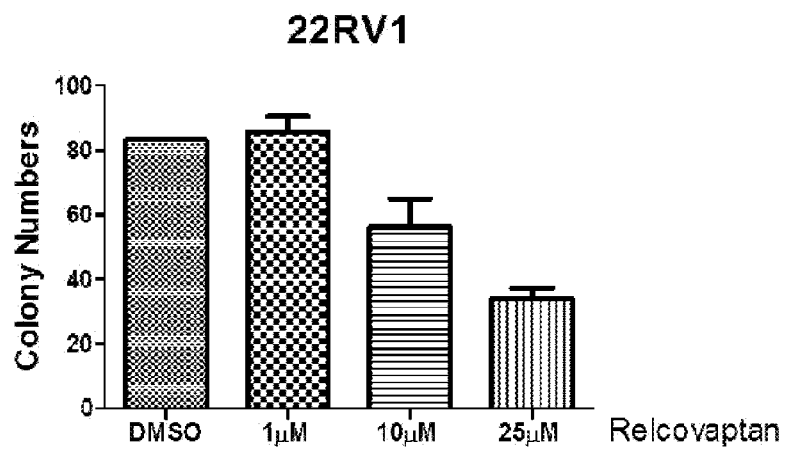
FIG. 17 shows that AVPR1a antagonist Relcovaptan inhibits prostate cancer cell anchorage independent growth.

Example 10—Relcovaptan Inhibits Prostate Cancer Cell Anchorage Independent Growth The effect of an AVPR1a antagonist on the anchorage independent growth of a castration-resistant prostate cancer cell line (i.e., 22Rv1) was evaluated. Briefly, 22Rv1, VCaP and RWPE1 cells were treated with 10 µM or 25 µM Relcovaptan (an AVPR1a antagonist) for six days followed by live cell counting. Results indicated that Relcovaptan inhibited prostate cancer cell anchorage independent growth. See FIG. 17.

Example 10—Relcovaptan Blocks Stimulation of ERK Phosphorylation by Arginine Varopressin (AVP)

Figure 18:
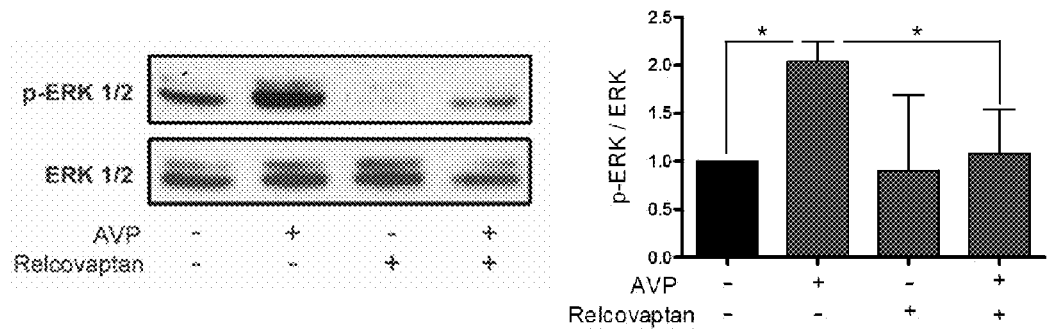
FIG. 18 shows that Relcovaptan blocks ERK signaling stimulated by ABP.

Total and phosphoERK levels were assessed following stimulation of 22Rv1 with 10 nM AVP for 25 minutes and pretreatment with AVPR1a antagonist (or vehicle control). Consistent with AVP stimulation of CRPC proliferation, AVP treatment results in increased phosphoERK levels. Results indicated that the effect is blocked by the AVPR1a subtype selective antagonist, relcovaptan (SR49059). See FIG. 18.

Example 11—AVPR1a Antagonism Blocks Growth of Newly CRPS Tumors In Vivo

Figure 19:
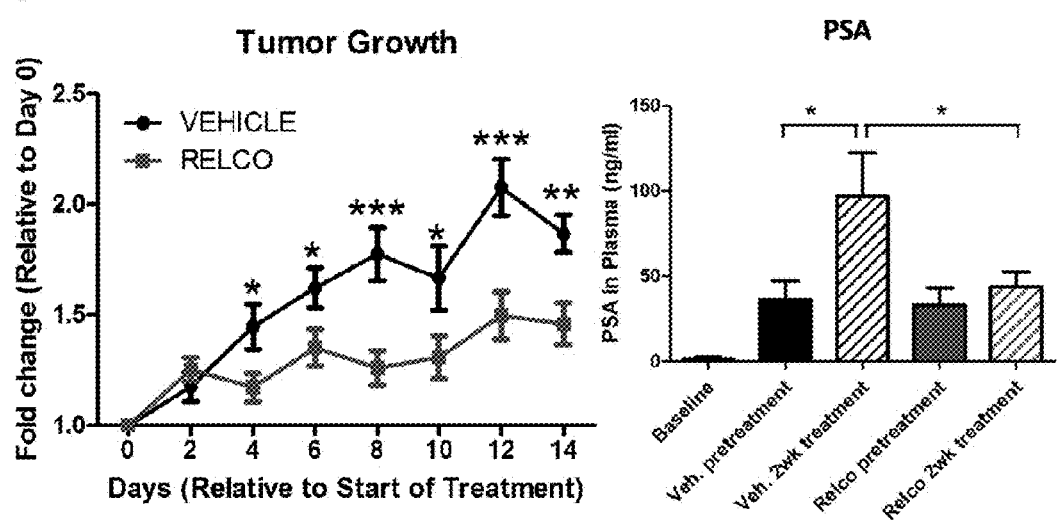
FIG. 19 shows that oral Relcovaptan slows growth of VCaP tumors in mice.

Subcutaneous VCaP xenografts (bilateral) were established in SCID mice. Mice were castrated when tumors reached 250-300 mm$^3$. Relcovaptan (TX) (n=13) or vehicle (n=10) was initiated seven days after castration (CX) for 14 days. Relcovaptan was given at 50 mg/kg daily through oral gavage. Circulating prostate specific antigen (PSA) was measured by ELISA in mice prior to tumor xenografting (baseline), at the time of castration (pre-treatment) and at the time of sacrifice (post-treatment). Results indicated that Relcovaptan significantly slowed the growth of castration resistant VCaP xenografts (left panel) and resulted in stabilization of PSA levels (right panel). See FIG. 19. There was no loss of weight in the drug treatment group compared to controls.

REFERENCES CITED

1. Brouard, R., Laporte, V., Serradeil Le Gal, C., Pignol, R., Jang, H., Donat, F., Lockwood, G., Fournie, D., and Dreux, F. (1998). Safety, tolerability, and pharmacokinetics of SR 49059, a V1a vasopressin receptor antagonist, after repeated oral administration in healthy volunteers. Advances in experimental medicine and biology 449, 455-465.
2. Decaux, G., Soupart, A., and Vassart, G. (2008). Non-peptide arginine-vasopressin antagonists: the vaptans. Lancet 371, 1624-1632.
3. Yap, T. A., Zivi, A., Omlin, A., and de Bono, J. S. (2011). The changing therapeutic landscape of castration-resistant prostate cancer. Nature reviews. Clinical oncology 8, 597-610.
4. Dehm, S. M., Schmidt, L. J., Heemers, H. V., Vessella, R. L., and Tindall, D. J. (2008). Splicing of a novel androgen receptor exon generates a constitutively active androgen receptor that mediates prostate cancer therapy resistance. Cancer Res 68, 5469-5477.
5. Guo, Z., Yang, X., Sun, F., Jiang, R., Linn, D. E., Chen, H., Chen, H., Kong, X., Melamed, J., Tepper, C. G., et al. (2009). A novel androgen receptor splice variant is upregulated during prostate cancer progression and promotes androgen depletion-resistant growth. Cancer Res 69, 2305-2313.
6. Li, Y., Chan, S. C., Brand, L. J., Hwang, T. H., Silverstein, K. A., and Dehm, S. M. (2013). Androgen Receptor Splice Variants Mediate Enzalutamide Resistance in Castration-Resistant Prostate Cancer Cell Lines. Cancer Res.
7. Mostaghel, E. A., Marck, B. T., Plymate, S. R., Vessella, R. L., Balk, S., Matsumoto, A. M., Nelson, P. S., and Montgomery, R. B. (2011). Resistance to CYP17A1 inhibition with abiraterone in castration-resistant prostate cancer: induction of steroidogenesis and androgen receptor splice variants. Clin Cancer Res 17, 5913-5925.
8. Rhodes D R, Yu J, Shanker K, Deshpande N, Varambally R, Ghosh D, Barrette T, Pandey A, Chinnaiyan A M. (2004) ONCOMINE: a cancer microarray database and integrated data-mining platform. Neoplasia. January-February; 6(1):1-6.
9. Chandran U R, Ma C, Dhir R, Bisceglia M, Lyons-Weiler M, Liang W, Michalopoulos G, Becich M, Monzon F A (2007) Gene expression profiles of prostate cancer reveal involvement of multiple molecular pathways in the metastatic process. BMC Cancer 7:64
10. Tamura K, Furihata M, Tsunoda T, Ashida S, Takata R, Obara W, Yoshioka H, Daigo Y, Nasu Y, Kumon H, Konaka H, Namiki M, Tozawa K, Kohri K, Tanji N, Yokoyama M, Shimazui T, Akaza H, Mizutani Y, Miki T, Fujioka T, Shuin T, Nakamura Y, Nakagawa H (2007) Molecular features of hormone-refractory prostate cancer cells by genome-wide gene expression profiles. Cancer Res 67:5117-5125
11. Lappano, R., and Maggiolini, M. (2011). G protein-coupled receptors: novel targets for drug discovery in cancer. Nature reviews. Drug discovery 10, 47-60.
12. Koshimizu, T. A., Nakamura, K., Egashira, N., Hiroyama, M., Nonoguchi, H., and Tanoue, A. (2012). Vasopressin V1a and V1b receptors: from molecules to physiological systems. Physiological reviews 92, 1813-1864.
13. Lemmens-Gruber, R., and Kamyar, M. (2006). Vasopressin antagonists. Cellular and molecular life sciences: CMLS 63, 1766-1779.
14. North W G, Fay M J, Longo K A, Du J. (1998) Expression of all known vasopressin receptor subtypes by small cell tumors implies a multifaceted role for this neuropeptide. Cancer Res. May 1; 58(9):1866-71.
15. North W G, Fay M J, Du J. (1999) MCF-7 breast cancer cells express normal forms of all vasopressin receptors plus an abnormal V2R. Peptides 20(7):837-42.
16. Manning M, Misicka A, Olma A, Bankowski K, Stoev S, Chini B, Durroux T, Mouillac B, Corbani M, Guillon G. (2012) Oxytocin and vasopressin agonists and antagonists as research tools and potential therapeutics. J Neuroendocrinol. April; 24(4):609-28.
17. Serradeil-Le Gal, C., Wagnon, J., Garcia, C., Lacour, C., Guiraudou, P., Christophe, B., Villanova, G., Nisato, D., Maffrand, J. P., Le Fur, G., et al. (1993). Biochemical and pharmacological properties of SR 49059, a new, potent, nonpeptide antagonist of rat and human vasopressin V1a receptors. The Journal of clinical investigation 92, 224-231.
18. Steinwall M, Bossmar T, Brouard R, Laudanski T, Olofsson P, Urban R, Wolff K, Le-Fur G, Akerlund M. The effect of relcovaptan (SR 49059), an orally active vasopressin V1a receptor antagonist, on uterine contractions in preterm labor. Gynecol Endocrinol. 2005 February; 20(2):104-9. PubMed PMID: 15823830.
19. Thibonnier M, Kilani A, Rahman M, DiBlasi T P, Warner K, Smith M C, Leenhardt A F, Brouard R. Effects of the nonpeptide V(1) vasopressin receptor antagonist SR49059 in hypertensive patients. Hypertension. 1999 December; 34(6):1293-300.
20. Tribollet E, Raufaste D, Maffrand J, Serradeil-Le Gal C. Binding of the non-peptide vasopressin V1a receptor antagonist SR-49059 in the rat brain: an in vitro and in vivo autoradiographic study. Neuroendocrinology. 1999 February; 69(2):113-20.
21. Peacock, S. O., Fahrenholtz, C. D., and Burnstein, K. L. (2012). Vav3 enhances androgen receptor splice variant activity and is critical for castration-resistant prostate cancer growth and survival. Mol Endocrinol 26, 1967-1979.
22. Iannucci N B, Ripoll G V, Garona J, Cascone O, Ciccia G N, Gomez D E, Alonso D F. Antiproliferative effect of 1-deamino-8-D-arginine vasopressin analogs on human breast cancer cells. Future Med Chem. 2011 December; 3(16):1987-93.
23. Sobel, R. E., and Sadar, M. D. (2005a). Cell lines used in prostate cancer research: a compendium of old and new lines—part 1. J Urol 173, 342-359.
24. Sobel, R. E., and Sadar, M. D. (2005b). Cell lines used in prostate cancer research: a compendium of old and new lines—part 2. J Urol 173, 360-372.
25. Korenchuk S, Lehr J E, MClean L, Lee Y G, Whitney S, Vessella R, Lin D L, Pienta K J. VCaP, a cell-based model system of human prostate cancer. In Vivo. 2001 March-April; 15(2):163-8.
26. Fahrenholtz, C. D., Beltran, P., and Burnstein, K. L. (2013). Targeting IGF-1R with ganitumab inhibits tumorigenesis and increases durability of response to androgen-deprivation therapy in VCaP prostate cancer xenografts. Molecular Cancer Therapeutics 12:394-404
27. Rao, S., Lyons, L. S., Fahrenholtz, C. D., Wu, F., Farooq, A., Balkan, W., and Burnstein, K. L. (2012). A novel nuclear role for the Vav3 nucleotide exchange factor in androgen receptor coactivation in prostate cancer. Oncogene 31, 716-727.
28. Rubin M A, Maher C A, Chinnaiyan A M. Common gene rearrangements in prostate cancer. J Clin Oncol. 2011 Sep. 20; 29(27):3659-68. doi: 10.1200/JCO.2011.35.1916. Epub 2011 Aug. 22.
29. Watson, P. A., Chen, Y. F., Balbas, M. D., Wongvipat, J., Socci, N. D., Viale, A., Kim, K., and Sawyers, C. L. (2010). Constitutively active androgen receptor splice variants expressed in castration-resistant prostate cancer require full-length androgen receptor. Proc Natl Acad Sci USA 107, 16759-16765.
30. Deocampo N D, Huang H, Tindall D J. The role of PTEN in the progression and survival of prostate cancer. Minerva Endocrinol. 2003 June; 28(2):145-53.
31. Wang M, Stearns M E 1991 Isolation and characterization of PC-3 human prostatic tumor sublines which preferentially metastasize to select organs in S.C.I.D. mice. Differentiation 48:115-125
32. Nishimura A, Kitano K, Takasaki J, Taniguchi M, Mizuno N, Tago K, Hakoshima T, Itoh H. Structural basis for the specific inhibition of heterotrimeric Gq protein by a small molecule. Proc Natl Acad Sci USA. 2010 Aug. 3; 107(31):13666-71.
33. Perkins L M, Payne A H. Quantification of P450scc, P450(17) alpha, and iron sulfur protein reductase in Leydig cells and adrenals of inbred strains of mice. Endocrinology. 1988 December; 123(6):2675-82.
34. Manaenko, A., Fathali, N., Khatibi, N. H., Lekic, T., Shum, K. J., Martin, R., Zhang, J. H., and Tang, J. (2011). Post-treatment with SR49059 improves outcomes following an intracerebral hemorrhagic stroke in mice. Acta neurochirurgica. Supplement 111, 191-196.

35. Kostrzewska, A., Laudanski, T., Steinwall, M., Bossmar, T., Serradeil-Le Gal, C., and Akerlund, M. (1998). Effects of the vasopressin V1a receptor antagonist, SR 49059, on the response of human uterine arteries to vasopressin and other vasoactive substances. Acta obstericia et gynecologica Scandinavica 77, 3-7.

36. Lyons, L. S., Rao, S., Balkan, W., Faysal, J., Maiorino, C. A., and Burnstein, K. L. (2008). Ligand-independent activation of androgen receptors by Rho GTPase signaling in prostate cancer. Mol Endocrinol 22, 597-608.

37. Fahrenholtz C D, Rick F G, Garcia M I, Zarandi M, Cai R Z, Block N L, Schally A V, Burnstein K L (2014) Preclinical efficacy of growth hormone-releasing hormone antagonists for androgen-dependent and castration-resistant human prostate cancer. Proc Natl Acad Sci USA. January 6. [Epub ahead of print] PubMed PMID: 24395797.

38. Ishteiwy R A, Ward T M, Dykxhoorn D M, Burnstein K L. (2012) The microRNA-23b/-27b cluster suppresses the metastatic phenotype of castration-resistant prostate cancer cells. PLoS One 7(12):e52106.

39. Scatena C D, Hepner M A, Oei Y A, Dusich J M, Yu S F, Purchio T, Contag P R, Jenkins D E (2004) Imaging of bioluminescent LNCaP-luc-M6 tumors: a new animal model for the study of metastatic human prostate cancer. Prostate 59:292-303

40. Jenkins D E, Yu S F, Hornig Y S, Purchio T, Contag P R 2003 In vivo monitoring of tumor relapse and metastasis using bioluminescent PC-3M-luc-C6 cells in murine models of human prostate cancer. Clin Exp Metastasis 20:745-756

41. Havens A M, Pedersen E A, Shiozawa Y, Ying C, Jung Y, Sun Y, Neeley C, Wang J, Mehra R, Keller E T, McCauley L K, Loberg R D, Pienta K J, Taichman R S. (2008) An in vivo mouse model for human prostate cancer metastasis. Neoplasia. April; 10(4):371-80.

42. Park S I, Kim S J, McCauley L K, Gallick G E Pre-clinical mouse models of human prostate cancer and their utility in drug discovery. Curr Protoc Pharmacol Chapter 14:Unit 14 15

43. Bockaert, J., L. Fagni, A. Dumuis, and P. Marin, GPCR interacting proteins (GIP). Pharmacol Ther, 2004. 103(3): 203-221.

44. Bockaert, J., J. Perroy, C. Becamel, P. Marin, and L. Fagni, GPCR interacting proteins (GIPs) in the nervous system: Roles in physiology and pathologies Annu Rev Pharmacol Toxicol, 2010. 50: 89-109.

45. Lefkowitz, R. J., Seven transmembrane receptors: something old, something new. Acta Physiol (Oxf), 2007. 190(1): 9-19.

46. Lefkowitz, R. J. and S. K. Shenoy, Transduction of receptor signals by beta-arrestins. Science, 2005. 308 (5721): 512-517.

47. Zhu W, Tilley D G, Myers V D, Coleman R C, Feldman A M. Arginine vasopressin enhances cell survival via a G protein-coupled receptor kinase 2/β-arrestin1/extracellular-regulated kinase 1/2-dependent pathway in H9c2 cells. Mol Pharmacol. 2013 August; 84(2):227-35. doi: 10.1124/mol.113.086322.

48. Kim J I, Chakraborty P, Wang Z, Daaka Y. G-protein coupled receptor kinase 5 regulates prostate tumor growth. J Urol. 2012 January; 187(1):322-9.

49. Magnon C, Hall S J, Lin J, Xue X, Gerber L, Freedland S J, Frenette P S. Autonomic nerve development contributes to prostate cancer progression. Science. 2013 Jul. 12; 341(6142):1236361.

50. Gaj T, Gersbach C A, Barbas C F 3rd. ZFN, TALEN, and CRISPR/Cas-based methods for genome engineering. Trends Biotechnol. 2013 July; 31(7):397-405.

51. Cai C, He H H, Chen S, Coleman I, Wang H, Fang Z, Chen S, Nelson P S, Liu X S, Brown M, Balk S P. Androgen receptor gene expression in prostate cancer is directly suppressed by the androgen receptor through recruitment of lysine-specific demethylase 1. Cancer Cell. 2011 Oct. 18; 20(4):457-71.

---

What is claimed is:

1. A method of treating metastatic prostate cancer in a mammalian subject consisting of administering a composition consisting of an arginine vasopressin receptor (AVPR) 1a antagonist that selectively inhibits AVPR1a and not AVPR1b or AVPR2 to a mammalian subject having an AVRP1a-expressing prostate cancer in an amount effective to treat the metastatic prostate cancer.

2. The method of claim 1, wherein the AVPR1a antagonist is selected from the group consisting of a small molecule, an antibody, a peptide antagonist and an oligonucleotide antagonist.

3. The method of claim 1, wherein the AVPR1a antagonist is selected from the group consisting of Relcovaptan, OPC-21268, PF-00738245, SRX-251, SRX-246, Conivaptan, Nelivaptan, Lixivaptan, Mozavaptan, Satavaptan, Tolvaptan and demeclocycline.

4. The method of claim 1, wherein the AVPR1a antagonist is Relcovaptan.

5. A method of decreasing the proliferation or metastasis of prostate cancer cells in a mammalian subject having metastatic prostate cancer, consisting of contacting the cells with a composition consisting of an arginine vasopressin receptor (AVPR) 1a antagonist that selectively inhibits AVPR1a and not AVPR1b or AVPR2 to in an amount effective to decrease proliferation or metastasis of the cancer cells in the subject.

6. The method of 5, wherein the AVPR1a antagonist is selected from the group consisting of a small molecule, an antibody, a peptide antagonist and an oligonucleotide antagonist.

7. The method of claim 5, wherein the AVPR1a antagonist is selected from the group consisting of Relcovaptan, OPC-21268, PF-00738245, SRX-25 and SRX-246.

8. The method of claim 7, wherein the AVPR1a antagonist is Relcovaptan.

9. A method of treating metastatic prostate cancer in a mammalian subject consisting of administering a composition consisting of an arginine vasopressin receptor (AVPR) 1a antagonist that selectively inhibits AVPR1a and not AVPR1b or AVPR2 to a mammalian subject having an AVRP1a-expressing prostate cancer in an amount effective to treat the metastatic prostate cancer; and a composition consisting of a therapeutic selected from the group consisting of an androgen receptor antagonist, an inhibitor of androgen synthesis, a gonadotropin-releasing hormone (GnRH) agonist and a GnRH antagonist.

10. The method of claim 9, wherein the androgen receptor antagonist is selected from the group consisting of Enzalutamide, Bicalutamide, Ostarine, Flutamide, Cyproterone acetate, Gugguisterone, Nilutamide, PF998245, (R)-Bicalutamide, 1,1-Dichloro-2,2-bis(4-chlorophenyl)ethene, ARN-509 and MDV-3100.

11. The method of claim 9, wherein the inhibitor of androgen synthesis is Abiraterone acetate.

12. The method of claim 9, wherein the GnRH agonist is selected from the group consisting of leuprolide, buserelin, histrelin, goserelin and deslorelin.

13. The method of claim 9, wherein the GnRH antagonist is selected from the group consisting of cetrorelix, ganirelix, abarelix and degarelix.

* * * * *

UNITED STATES PATENT AND TRADEMARK OFFICE
CERTIFICATE OF CORRECTION

Page 1 of 1

PATENT NO. : 10,231,952 B2
APPLICATION NO. : 14/811354
DATED : March 19, 2019
INVENTOR(S) : Kerry L. Burnstein It is certified that error appears in the above-identified patent and that said Letters Patent is hereby corrected as shown below:

In the Specification

Column 1, Lines 16-20, please delete:
"This invention was made with government support under Grant Number R01 CA132200 awarded by the National Cancer Institute and Grant Number F30AG038275 awarded by the National Institute on Aging. The government has certain rights in the invention."

And insert:
-- This invention was made with government support under grant numbers CA132200 and AG038275 awarded by the National Institutes of Health. The government has certain rights in the invention. --

Signed and Sealed this
Twenty-fifth Day of February, 2020

Andrei Iancu
*Director of the United States Patent and Trademark Office*

SEQUENCE LISTING

```
<160> NUMBER OF SEQ ID NOS: 7

<210> SEQ ID NO 1
<211> LENGTH: 418
<212> TYPE: PRT
<213> ORGANISM: Homo sapiens
<300> PUBLICATION INFORMATION:
<308> DATABASE ACCESSION NUMBER: NCBI / NP_000697.1
<309> DATABASE ENTRY DATE: 2014-05-05
<313> RELEVANT RESIDUES IN SEQ ID NO: (1)..(418)

<400> SEQUENCE: 1

Met Arg Leu Ser Ala Gly Pro Asp Ala Gly Pro Ser Gly Asn Ser Ser
1               5                   10                  15

Pro Trp Trp Pro Leu Ala Thr Gly Ala Gly Asn Thr Ser Arg Glu Ala
                20                  25                  30

Glu Ala Leu Gly Glu Gly Asn Gly Pro Pro Arg Asp Val Arg Asn Glu
            35                  40                  45

Glu Leu Ala Lys Leu Glu Ile Ala Val Leu Ala Val Thr Phe Ala Val
        50                  55                  60

Ala Val Leu Gly Asn Ser Ser Val Leu Leu Ala Leu His Arg Thr Pro
65                  70                  75                  80

Arg Lys Thr Ser Arg Met His Leu Phe Ile Arg His Leu Ser Leu Ala
                85                  90                  95
```

-continued

```
Asp Leu Ala Val Ala Phe Phe Gln Val Leu Pro Gln Met Cys Trp Asp
                100                 105                 110
Ile Thr Tyr Arg Phe Arg Gly Pro Asp Trp Leu Cys Arg Val Val Lys
            115                 120                 125
His Leu Gln Val Phe Gly Met Phe Ala Ser Ala Tyr Met Leu Val Val
        130                 135                 140
Met Thr Ala Asp Arg Tyr Ile Ala Val Cys His Pro Leu Lys Thr Leu
145                 150                 155                 160
Gln Gln Pro Ala Arg Arg Ser Arg Leu Met Ile Ala Ala Ala Trp Val
                165                 170                 175
Leu Ser Phe Val Leu Ser Thr Pro Gln Tyr Phe Val Phe Ser Met Ile
            180                 185                 190
Glu Val Asn Asn Val Thr Lys Ala Arg Asp Cys Trp Ala Thr Phe Ile
        195                 200                 205
Gln Pro Trp Gly Ser Arg Ala Tyr Val Thr Trp Met Thr Gly Gly Ile
210                 215                 220
Phe Val Ala Pro Val Val Ile Leu Gly Thr Cys Tyr Gly Phe Ile Cys
225                 230                 235                 240
Tyr Asn Ile Trp Cys Asn Val Arg Gly Lys Thr Ala Ser Arg Gln Ser
                245                 250                 255
Lys Gly Ala Glu Gln Ala Gly Val Ala Phe Gln Lys Gly Phe Leu Leu
            260                 265                 270
Ala Pro Cys Val Ser Ser Val Lys Ser Ile Ser Arg Ala Lys Ile Arg
        275                 280                 285
Thr Val Lys Met Thr Phe Val Ile Val Thr Ala Tyr Ile Val Cys Trp
290                 295                 300
Ala Pro Phe Phe Ile Ile Gln Met Trp Ser Val Trp Asp Pro Met Ser
305                 310                 315                 320
Val Trp Thr Glu Ser Glu Asn Pro Thr Ile Thr Ile Thr Ala Leu Leu
                325                 330                 335
Gly Ser Leu Asn Ser Cys Cys Asn Pro Trp Ile Tyr Met Phe Phe Ser
            340                 345                 350
Gly His Leu Leu Gln Asp Cys Val Gln Ser Phe Pro Cys Cys Gln Asn
        355                 360                 365
Met Lys Glu Lys Phe Asn Lys Glu Asp Thr Asp Ser Met Ser Arg Arg
370                 375                 380
Gln Thr Phe Tyr Ser Asn Asn Arg Ser Pro Thr Asn Ser Thr Gly Met
385                 390                 395                 400
Trp Lys Asp Ser Pro Lys Ser Ser Lys Ser Ile Lys Phe Ile Pro Val
                405                 410                 415
Ser Thr
```

```
<210> SEQ ID NO 2
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 2
ggtatgtgga aggactcgcc taaatcttc                                        29

<210> SEQ ID NO 3
<211> LENGTH: 29
<212> TYPE: DNA
<213> ORGANISM: Artificial Sequence
```

```
<220> FEATURE:
<223> OTHER INFORMATION: Synthetic oligonucleotide

<400> SEQUENCE: 3
tctccatgat cgaggtgaac aatgtcacc                                    29

<210> SEQ ID NO 4
<211> LENGTH: 64
<212> TYPE: DNA
<213> ORGANISM: Artificial Sequence
<220> FEATURE:
<223> OTHER INFORMATION: Synthetic oligonucleotide

<400> SEQUENCE: 4
ggtatgtgga aggactcgcc taaatcttcc tcgaggaaga tttaggcgag tccttccaca   60
tacc                                                               64

<210> SEQ ID NO 5
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 5
gcaagctgac cctgaagttc atctcttgaa tgaacttcag ggtcagcttg c            51

<210> SEQ ID NO 6
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 6
gcaagctgac cctgaagttc attcaagaga tgaacttcag ggtcagcttg c            51

<210> SEQ ID NO 7
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 7
ccgggctttg tctaacataa gacctcgagg tcttatgtta gacaaagctt tttg         54
```